United States Patent
Ito et al.

(10) Patent No.: US 8,581,018 B2
(45) Date of Patent: Nov. 12, 2013

(54) ABSORBER COMPRISING PULP, TEA DREGS AND WATER ABSORBENT RESIN; SANITARY ARTICLES USING THE ABSORBER AND PRODUCTION METHOD THEREOF

(75) Inventors: Hiroshi Ito, Tokyo (JP); Kouichi Fukuda, Tokyo (JP)

(73) Assignee: Daiki Co., Ltd. (JP)

( * ) Notice: Subject to any disclaimer, the term of this patent is extended or adjusted under 35 U.S.C. 154(b) by 785 days.

(21) Appl. No.: 12/529,028

(22) PCT Filed: Mar. 3, 2008

(86) PCT No.: PCT/JP2008/054221
§ 371 (c)(1),
(2), (4) Date: Jun. 17, 2010

(87) PCT Pub. No.: WO2008/108476
PCT Pub. Date: Sep. 12, 2008

(65) Prior Publication Data
US 2010/0249737 A1    Sep. 30, 2010

(30) Foreign Application Priority Data
Mar. 1, 2007  (JP) ................................ 2007-052102

(51) Int. Cl.
*A61F 13/15* (2006.01)
*A61F 13/53* (2006.01)

(52) U.S. Cl.
USPC ........................... 604/359; 604/367; 604/674

(58) Field of Classification Search
USPC ......................................... 604/365–377, 359
See application file for complete search history.

(56) References Cited

U.S. PATENT DOCUMENTS 4,902,463 A * 2/1990 Tanaka et al. ................. 264/122
6,294,118 B1 * 9/2001 Huber et al. ................... 264/118

(Continued)

FOREIGN PATENT DOCUMENTS

| JP | 2-107250 | 4/1990 |
| JP | 11-001896 | 1/1999 |
| JP | 2002-114617 | 4/2002 |
| JP | 2002-285021 | 10/2002 |

(Continued)

OTHER PUBLICATIONS

International Search Report mailed Jun. 17, 2008 in corresponding PCT International Application No. PCT/JP2008/054221.

*Primary Examiner* — Jackie Ho
*Assistant Examiner* — Kathryn E Ditmer
(74) *Attorney, Agent, or Firm* — Ostrolenk Faber LLP

(57) ABSTRACT

An absorber wherein crushed tea leaves having a particle size of 0.05 to 4.6 mm are dispersed and held within a pulp fiber material having a fiber length of 0.1 to 7 mm, for water-absorbing, drying, and odor-eliminating with good visual quality, and maintaining sanitary conditions, and sanitary articles using the absorber. An upper water-absorbing paper layer portion forms an upper surface, a lower water-absorbing paper layer portion forms a lower surface, and a water-absorbing mixture layer portion is provided between the upper water-absorbing paper layer portion. The layer portions are overlapped and integrated forming the absorber. The water-absorbing mixture layer portion is formed by including a crushed pulp fiber material beaten to have a fiber length of 0.1 to 7 mm, and crushed tea dregs having a particle size of 0.7 to 3.8 mm in mixing content percentage of 14 to 43% by weight.

18 Claims, 6 Drawing Sheets

(56) References Cited

U.S. PATENT DOCUMENTS

| | | | |
|---|---|---|---|
| 2003/0004479 A1* | 1/2003 | Ueda et al. | 604/359 |
| 2004/0048955 A1* | 3/2004 | Wada et al. | 524/9 |
| 2006/0135922 A1* | 6/2006 | Dovertie | 604/368 |
| 2008/0167634 A1* | 7/2008 | Kouta et al. | 604/367 |

FOREIGN PATENT DOCUMENTS

| | | |
|---|---|---|
| JP | 2003-154588 | 5/2003 |
| JP | 2004-089234 | 3/2004 |
| JP | 2004-137661 | 5/2004 |
| JP | 2006-341105 | 12/2006 |

* cited by examiner

US 8,581,018 B2

ABSORBER COMPRISING PULP, TEA DREGS AND WATER ABSORBENT RESIN; SANITARY ARTICLES USING THE ABSORBER AND PRODUCTION METHOD THEREOF

CROSS-REFERENCE TO RELATED APPLICATIONS

The present application is a 35 U.S.C. §§371 national phase conversion of PCT/JP2008/054221, filed Mar. 3, 2008, which claims priority of Japanese Patent Application No. 2007-052102, filed Mar. 1, 2007. The PCT International Application was published in the Japanese language.

TECHNICAL FIELD

The present invention relates to an absorber and sanitary articles using the absorber that have water-absorbing function, liquid-absorbing function, oil-absorbing function, odor-eliminating function, and bacterial growth-inhibitory function and are widely used for humans, animals or others; in particular, to an absorber being used widely for humans, animals or others which need hygienically and environmentally water-absorbing action, liquid-absorbing action, oil-absorbing action, odor-eliminating action, and bacterial growth-inhibitory action and to a method of producing the absorber, and to sanitary articles using the absorber; and a method of producing the sanitary article. The present invention also relates to an absorber which can maintain sanitary conditions over a long time, and is used widely for humans, animals or others and is required for water-absorbing property, liquid-absorbing property, oil-absorbing property, odor-eliminating property, or bacterial growth-inhibitory action thereof over long time, and is widely used for humans, animals or others, and to a method of producing the absorber, and to sanitary articles using the absorber and to a method of producing the sanitary article; in particular to an absorber which contains tea leaves, can maintain sanitary conditions for a long time, and is widely used for humans, animals or others; and to a method of producing the absorber; and to also sanitary articles using the absorber, such as sheets for animals and auxiliary nursing-care mats. Furthermore, the present invention relates to a sanitary article required for water-absorbing property such as absorbers, sheet for humans or animals, auxiliary bedding sheet, auxiliary nursing-care mat, disposable diaper, disposable diaper for animals, sanitary napkin, sanitary napkin for animals, breast pad, sweat pad, and urine pad; a method of producing the sanitary article; an absorber usable for the sanitary article; and a method of producing the absorber. Still further, the present invention relates to a sanitary article required for water-absorbing property and used for humans or animals; a method of producing the sanitary article; in particular to a disposable sanitary article used for humans or animals that can maintain sanitary conditions even under prolonged use and are excellent in various functions as sanitary articles such as infiltration velocity, drying velocity, spot property, and water-absorbing amount; and a method of producing the sanitary article. Still further, the present invention relates to an absorber that can be used for a sanitary article such as sheet, auxiliary bedding sheet, auxiliary nursing-care mat, disposable diaper, disposable diaper for animals, sanitary napkin, sanitary napkin for animals, breast pad, sweat pad, and urine pad and is widely used for humans, animals or others; a method of producing the absorber; a sanitary article using the absorber, is required for water-absorbing property, and is used for humans or animals; and a method of producing the sanitary article.

BACKGROUND ART

An absorber, which contains an absorbable material and a water-absorbing resin and is formed into sheet-like, for example, is used for sanitary articles required for water absorbing property such as sheet, auxiliary bedding sheet, auxiliary nursing-care mat, sheet for animals (sheet for pets), disposable diaper, disposable diaper for animals, sanitary napkin, sanitary napkin for animals, breast pad, sweat pad, and urine pad, for example. The absorber is used for an absorbing portion of disposable diaper, breast pad, sweat pad, incontinence pad, sheet, auxiliary nursing-care mat or sheet for pets, auxiliary bedding sheet, or sanitary napkin, for example. Among these, disposable diapers and incontinence pads are used as excrement treating materials for humans, in particular for child-care, advancing age, or ailing persons, and are desired for excellent antibacterial action to inhibit proliferation of bacteria such as *Pseudomonas aeruginosa, Staphylococcus aureus, Legionella pneumophila*, and *Streptococcus* in addition to excellent water-absorbing action and odor-eliminating action. Furthermore, sheets for pets are used as excrement treating materials for animals and are desired for water-absorbing action, odor-eliminating action, and antibacterial action. Auxiliary nursing-care mats are intended to absorb or treat excretory substances leaked from disposable diapers or incontinence pads, are desired for function to maintain proper sanitary conditions of beds, bedclothes, etc. and to prevent their blots, and are desired for water-absorbing action, odor-eliminating action, and antibacterial action. Bedding aid mats are used for mild bed-bound ailing persons, for example, and are desired for odor-eliminating action to body odor and antibacterial action.

Furthermore, moisture other than sweat is continuously evacuating out of human skin even while asleep, the moisture is absorbed by bedclothes or night clothes, therefore, heat-retaining property and moderate hygroscopic property and water-absorbing property are required, and even as for sanitary articles, heat-retaining property and hygroscopic property, in particular good skin feeling are required since being usually worn on bodies.

As described above, sanitary articles have various functions desired differently depending on applications; auxiliary nursing-care mats, diapers, bedclothes, and incontinence pads have been formed from fibers having high hygroscopic property and water-absorbing property, thus are likely to be contaminated by depositing horny layers dropped from skin surface and cornified, scurf due to skin sebum or sweat with dusts on skin, etc., pathogenic bacteria tend to proliferate, which is a problem particularly in a case of decubitus ulcer, etc.

Consequently, the auxiliary nursing-care mats, diapers, bedclothes, and incontinence pads use cotton, etc. with washing resistance as a raw material so that cleanliness is always maintained in order to always maintain purity and they can be used repeatedly while frequently exchanging them.

The auxiliary nursing-care mats and diapers made of cotton, etc. are washed at each exchange; however, it is necessary to select insufficiently clean sheets and wash again them in order to make all sheets clean in a desirable level since they are relatively bulky, the sheets have respectively different contamination levels, and cleanable levels by washing are different due to mechanical washing by laundry machines, which is troublesome since much labor hours are necessary. Accordingly, the present inventors have proposed a disposal absorber and a sanitary article using the absorber, wherein a dry material of leach liquor of tea dregs of green tea, oolong tea, and red tea and tea dregs are included into water-absorbing paper or nonwoven fabric to inhibit the proliferation of *Pseudomonas aeruginosa*, *Staphylococcus aureus*, *Legionella pneumophila*, and *Streptococcus* for 24 hours, thereby the cleanliness of the sanitary article can be maintained for a long period from in use (see Japanese Unexamined Patent Publication Hei No. 11-1896).

In addition, absorbers have conventionally been noticed with respect to water-absorbing property and the performance has been focused on water-absorbing property during a shorter period, thus absorbers are produced to have a large water-absorbing velocity. When tea dregs are mixed in order to give an odor-eliminating property, however, there arises a problem to decrease the water-absorbing velocity.

DISCLOSURE OF THE INVENTION

Problems to be Solved by the Invention

In a case of a disposal absorber or a sanitary article using the absorber that has a water-absorbing mixture layer portion formed by supporting a powder-like high water-absorption resin, a dry product of leach liquor from tea dregs (used tea leaves; the rest is omitted.) and crushed tea dregs on a crushed pulp fiber material, it is preferred that the fluctuation of odor-eliminating action and bacterial growth-inhibitory action and mixture non-uniformity of the tea dregs can be small, because the dry product of tea dregs-leach liquor obtained by leaching from tea dregs of green tea, oolong tea and black tea is included along with the tea dregs, the amount of mixed tea dregs can be reduced and mixture non-uniformity of the tea dregs of mixed tea dregs can be compensated by the dry product of tea dregs-leach liquor, it is necessary to leach the tea dregs by hot water and to filter the leach liquor and to dry the filtrate, it is unavoidable to increase by just that much, and it is problem.

It is an object of the present invention to solve the mixture non-uniformity of tea dregs mixture due to mixing the crushed tea dregs and decrease of water-absorbing velocity with respect to the disposal absorber or a sanitary article using the absorber that comprises a water-absorbing mixture layer portion formed by supporting a powder-like high water-absorbing resin and crushed tea dregs, or a powder-like high water-absorbing resin, a dry product of leach liquor of tea dregs, and crushed tea dregs on a crushed pulp fiber material.

Furthermore, in order to form the water-absorbing mixture layer portion of the absorber containing the crushed pulp fiber material, the crushed tea leaves, and the water-absorbing resin on a water-absorbing paper layer part formed with one or more sheet of thin paper or water-absorbing paper, the mixture of the crushed pulp fiber material, the water-absorbing resin, and the crushed tea leaves is disposed in a layer-shape on the thin paper, a negative pressure is applied from under the thin paper to aspirate, and the disposed water-absorbing mixture layer portion containing the mixture of the crushed pulp fiber material, the water-absorbing resin, and the crushed tea leaves is formed on the thin paper in a uniform thickness thereby to produce the absorber. However, in this case, when the crushed tea leaves are not uniformly mixed into the mixture of the crushed pulp fiber material, the water-absorbing resin, and the crushed tea leaves, the crushed pulp fiber material and the crushed tea leaves cause dispersion non-uniformity during forming the water-absorbing mixture layer portion, the crushed tea leaves particles cause bias of distribution due to non-uniformity of grain size, thus the odor-eliminating action and bacterial growth-inhibitory action come to non-uniform, which is a problem. When the crushed tea leaves are milled to a finer grain size in view of this problem, they are likely to accumulate at narrow sites between the particles of the crushed pulp fiber material, resulting in poor water-absorbing property of sheets; furthermore, the fine crushed tea leaves particles drop out of the water-absorbing mixture layer portion due to negative-pressure aspiration, the crushed tea leaves mix into an air intake duct, or the mixed crushed tea leaves mix into the water-absorbing mixture layer portion due to a cyclic usage of the air intake, resulting in more or less amount of the crushed tea leaves within the water-absorbing mixture layer portion compared to an intended amount or nonuniform distribution, which is a problem from the fluctuation of the odor-eliminating action and bacterial growth-inhibitory action within the water-absorbing mixture layer portion. When the grain size of the crushed tea leaves is made coarser in view of this problem, the crushed tea leaves particles do not enter into the crushed pulp fiber material layer, a great number of black particles tend to remain on the surface to represent a situation like fungus generation, resulting in a problem to degrade commercial value due to poor appearance.

It is another object of the present invention to solve the problem with respect to dispersion fluctuation of the crushed tea leaves and the problem with respect to the water-absorbing property in the absorber that includes the water-absorbing mixture layer portion where the crushed tea leaves and a water-absorbing resin are mixed in the crushed pulp fiber material or the sanitary article that uses the absorber.

The present inventors have found that the selection of raw materials is facilitated when producing the absorbers depending on the applications by means of segmentalizing the water-absorbing performance of the absorbers into the items of "infiltration velocity", "drying velocity", "return sheet number", "return amount", "spot property", and "water-absorbing amount" and measuring these items since the best water-absorbing property of the absorber is different depending on its application.

That is, for example, the sanitary article under a use mode to always directly contact skin such as disposable diaper and urine pad is required to have a large water-absorbing velocity and to take a surface-dry condition within a short period, therefore, it is necessary that the raw materials of the absorbers used for sanitary articles such as disposable diaper and urine pad are selected so that "infiltration velocity", "drying velocity", and "water-absorbing amount" are larger and "return sheet number" and "return amount" are smaller. On the other hand, the sanitary article under a use mode not to always directly contact skin such as auxiliary nursing-care mat and sheet for pets is required to have a large water-absorbing amount and to exert odor-eliminating function for a long period, therefore, it is necessary that the raw materials are selected so that "infiltration velocity", "drying velocity", and "water-absorbing amount" are larger and "spot property" is smaller even when the content of the crushed tea leaves is larger.

The present inventors have found that when absorbers and water-absorbing mixture layer portions of other sanitary articles, into which the crushed tea leaves are dispersed, are prepared in order to maintain the antibacterial effect and odor-eliminating effect in the absorbers or the sanitary articles using the absorber, such performance degrades as water-absorbing performance, infiltrating performance, return amount of moisture such as urine after use, and wetted spot size during use of the absorbers and sanitary articles by mixing the crushed tea leaves. The present inventors have also found that degradation of performance with respect to water-absorption of absorbers or sanitary articles using the absorber resulting from the existence of the crushed tea leaves in the absorbers or sanitary articles using the absorber is derived from the nonuniformity of size distribution due to the existence of fine crushed tea leaves particles. Consequently, the present inventors have found that the degradation of performance with respect to water-absorption of absorbers or sanitary articles using the absorber can be avoided by means of setting the particle size of the crushed pulp material particles of 0.1 mm or more to 7 mm or less so that fine crushed pulp fiber material particles with a particle size below 0.1 mm is removed and setting the particle size of the particle size of the crushed tea leaves to 0.05 mm to 4.6 mm so that fine crushed tea leaves with a particle size below 0.05 mm is removed. Furthermore, the present inventors have found that when the crushed pulp material particles and the crushed tea leaves are adjusted to have the particle size within these ranges and the mixture of the crushed pulp material particles and the crushed tea leaves, disposed on an thin paper (including tissue paper, toilet paper, sanitary paper and other; the rest is omitted.) moving by net conveyers, screen conveyers, etc., is aspirated from under the thin paper by a negative pressure, the crushed tea leaves can be mixed so that the crushed tea leaves are distributed less at upper portion and much from intermediate to lower portion of the water-absorbing mixture layer portion of the absorber and the leak of the crushed tea leaves can be reduced from the water-absorbing mixture layer portion. Still further, the present inventors have found that the content of the crushed tea leaves can be maintained constant in the water-absorbing mixture layer portion of the absorber containing the crushed tea leaves, and the odor-eliminating action and bacterial growth-inhibitory action can be stabilized in the absorber and sanitary articles using the absorber.

The present invention intends to provide an absorber having larger "infiltration (water penetration) velocity", "drying velocity", and "water-absorbing amount" of liquids such as water and urine by increasing the content of the crushed tea leaves in the water-absorbing mixture layer portion of the absorber.

Furthermore, the present inventors have found that since disposable diapers of one layer-type sanitary articles, urine pads, and absorbers used for them are desired to have larger "infiltration velocity", "water-absorbing amount", and "drying velocity", it is preferred in order to produce the absorbers that the crushed tea leaves to be mixed with the crushed pulp material with a particle size 0.1 mm to 7 mm are medium-coarse with a particle size 0.7 mm to 2.4 mm, in particular the crushed tea leaves are preferably medium-coarse with a particle size 1.2 mm to 1.7 mm. In regards to such crushed tea leaves, it has been found that the large-coarse crushed tea leaves with a particle size 1.2 mm to 4.6 mm are preferable; in particular the large-coarse crushed tea leaves with a particle size 2.6 mm to 3.4 mm are more preferable.

On the other hand, in cases of sheet for pets and auxiliary nursing-care mats of one layer-type sanitary articles, "infiltration velocity" and "drying velocity" are desired to be large, and "spot property" is desired to be small; it has been found in regards to the crushed tea leaves to be mixed that the relatively small crushed tea leaves with a particle size 0.05 mm to 0.6 mm are preferable, in particular, the relatively small crushed tea leaves with a particle size 0.1 mm to 0.3 mm are more preferable.

It is an object of the present invention to solve the problems in terms of water-absorbing property, drying property, cleaning property, or odor-eliminating property of absorbers or sanitary articles by suppressing the mixture non-uniformity at water-absorbing mixture layer portions containing a crushed pulp fiber material, crushed tea leaves, and a water-absorbing resin, in particular by suppressing the mixture non-uniformity of the crushed tea leaves, in disposal absorbers or sanitary articles where crushed tea leaves are mixed in order to maintain the cleanliness and odor-eliminating property for a long period of absorbers or sanitary articles using the absorber.

It is an object of the present invention to provide an absorber or a sanitary article using the absorber having superior water-absorbing performance, and odor-eliminating performance, exhibiting good appearance, and capable of maintaining sanitary conditions for relatively long periods by means of including crushed tea leaves through dispersing and sustaining in pulp fiber material.

That is, the present invention is an absorber formed by overlapping in layers and integrating an upper water-absorbing paper layer portion forming an upper surface, a lower water-absorbing paper layer portion forming a lower surface, and a water-absorbing mixture layer portion provided between the upper water-absorbing paper layer portion and the lower water-absorbing paper layer portion;

wherein the water-absorbing mixture layer portion is formed by including a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material;

in addition, the present invention is an absorber formed by overlapping in layers and integrating an upper water-absorbing paper layer portion forming an upper surface, a lower water-absorbing paper layer portion forming a lower surface, and a water-absorbing mixture layer portion provided between the upper water-absorbing paper layer portion and the lower water-absorbing paper layer portion;

wherein the water-absorbing mixture layer portion is formed by including a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material;

furthermore, the present invention is an absorber comprising an upper water-absorbing paper layer portion forming an upper surface, a lower water-absorbing paper layer portion forming a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a crushed pulp fiber material beaten to have a fiber length of 0.1 to 7 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still further, the present invention is an absorber, comprising an upper water-absorbing paper layer portion forming form an upper surface, a lower water-absorbing paper layer portion forming a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a crushed pulp fiber material beaten to have a fiber length of 0.1 to 7 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still additionally, the present invention is an absorber, comprising an upper water-absorbing paper layer portion forming an upper surface, a lower water-absorbing paper layer portion forming a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

in addition to these, the present invention is an absorber, comprising an upper water-absorbing paper layer portion forming an upper surface, a lower water-absorbing paper layer portion forming a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

besides these, the present invention is an absorber, comprising an upper water-absorbing paper layer portion forming an upper surface, a lower water-absorbing paper layer portion forming a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still besides these, the present invention is an absorber, comprising an upper water-absorbing paper layer portion to form an upper surface, a lower water-absorbing paper layer portion to form a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed.

In the absorber of the present invention, the water-absorbing mixture layer portion, upper water-absorbing mixture layer portion, and lower water-absorbing mixture layer portion may contain a dried material of a leach liquor obtained by leaching tea leaves and/or used tea leaves using water or hot water at normal temperature or higher.

And furthermore, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, and a water-absorbing mixture layer portion provided between the upper water-absorbing paper layer portion and the lower water-absorbing paper layer portion;

wherein the water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material; and the upper water-absorbing paper layer portion, the lower water-absorbing paper layer portion, and the water-absorbing mixture layer portion are overlapped in layers and integrally formed;

in addition, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, and a water-absorbing mixture layer portion provided between the upper water-absorbing paper layer portion and the lower water-absorbing paper layer portion;

wherein the water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a water-absorbing resin in an amount less than the crushed pulp fiber material, and a crushed plastic-containing material in an amount less than the crushed pulp fiber material, the upper water-absorbing paper layer portion, the lower water-absorbing paper layer portion, and the water-absorbing mixture layer portion are overlapped in layers and integrally formed;

furthermore, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a crushed pulp fiber material beaten to have a fiber length of 0.1 to 7 mm, the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still further, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a crushed pulp fiber material beaten to have a fiber length of 0.1 to 7 mm, the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a water-absorbing resin in an amount less than the crushed pulp fiber material, and a crushed plastic-containing material in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still additionally, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

in addition to these, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

besides these, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed;

still besides these, the present invention is a sanitary article, comprising a water-permeable layer part to form an upper surface, a plastic water-impermeable film portion to form a lower surface, an upper water-absorbing paper layer portion positioned to contact the lower surface of the water-permeable layer part, a lower water-absorbing paper layer portion positioned to contact the upper surface of the water-impermeable film portion, an intermediate water-absorbing paper layer portion positioned between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a water-absorbing resin in an amount less than the crushed pulp fiber material, and a crushed plastic-containing material in an amount less than the crushed pulp fiber material, and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and integrally formed.

In the sanitary article of the present invention, the water-absorbing mixture layer portion, upper water-absorbing mixture layer portion, and lower water-absorbing mixture layer portion may contain a dried material of a leach liquor obtained by leaching tea leaves and/or used tea leaves using water or hot water at normal temperature or higher.

And furthermore, the present invention is a method of producing an absorber, comprising:

disposing a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material on a lower water-absorbing paper layer portion formed of at least one sheet of water-absorbing paper while aspirating from below the lower water-absorbing paper layer portion to form a water-absorbing mixture layer portion containing the crushed pulp fiber material, the water-absorbing resin, and the crushed tea leaves;

forming an upper water-absorbing paper layer portion by disposing at least one sheet of water-absorbing paper on the water-absorbing mixture layer portion to form a stratified material overlapped with the upper water-absorbing paper layer portion, the water-absorbing mixture layer portion, and the lower water-absorbing paper layer portion; and press-shaping integrally the stratified material;

in addition, the present invention is a method of producing an absorber, comprising:

disposing a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material on a lower water-absorbing paper layer portion formed of at least one sheet of water-absorbing paper while aspirating from below the lower water-absorbing paper layer portion to form a water-absorbing mixture layer portion containing the crushed pulp fiber material, the crushed tea leaves, the water-absorbing resin, and the crushed plastic-containing material;

forming an upper water-absorbing paper layer portion by disposing at least one sheet of water-absorbing paper on the water-absorbing mixture layer portion to form a stratified material overlapped with the upper water-absorbing paper layer portion, the water-absorbing mixture layer portion, and the lower water-absorbing paper layer portion; and press-shaping integrally the stratified material;

furthermore, the present invention is a method of producing an absorber, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion;

wherein the upper water-absorbing mixture layer portion is formed from a crushed pulp fiber material beaten to have a fiber length of 0.1 to 7 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material;

still further, the present invention is a method of producing an absorber, comprising:

laying an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion;

wherein the upper water-absorbing mixture layer portion is formed from a crushed pulp fiber material beaten to have a fiber length of 0.1 to 7 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin;

still additionally, the present invention is a method of producing an absorber, comprising:

laying an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing paper layer portion, and the lower water-absorbing paper layer portion;

wherein the upper water-absorbing mixture layer portion is formed from a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a water-absorbing resin in an amount less than the crushed pulp fiber material;

still additionally, the present invention is a method of producing an absorber, comprising:

laying an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion;

wherein the upper water-absorbing mixture layer portion is formed from a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin;

in addition to these, the present invention is a method of producing an absorber, comprising:

laying an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion;

wherein the upper water-absorbing mixture layer portion is formed from a mixture of a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin;

still besides these, the present invention is a method of producing an absorber, comprising:

laying an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, and press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion;

wherein the upper water-absorbing mixture layer portion is formed from a mixture of a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm in an amount less than the crushed pulp fiber material, and a crushed plastic-containing material in an amount less than the crushed pulp fiber material, and the lower water-absorbing mixture layer portion is formed from a mixture containing a crushed pulp fiber material beaten to a fiber length of 0.1 to 7 mm, in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin.

In the method of producing an absorber of the present invention, the water-absorbing mixture layer portion, upper water-absorbing mixture layer portion, and lower water-absorbing mixture layer portion may contain a dried material of a leach liquor obtained by leaching tea leaves and/or used tea leaves using water or hot water at normal temperature or higher.

And besides these, the present invention is a method of producing a sanitary article, comprising:

forming a lower water-absorbing paper layer portion formed of at least one sheet of water-absorbing paper, disposing a mixture containing a crushed pulp fiber material beaten to a fiber length of 0.1 to 7 mm, in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material on the lower water-absorbing paper layer portion while aspirating from below the lower water-absorbing paper layer portion to form a water-absorbing mixture layer portion containing the crushed pulp fiber material, the crushed tea leaves, and the water-absorbing resin, disposing an upper water-absorbing paper layer portion formed of at least one sheet of water-absorbing paper on the water-absorbing mixture layer portion, pressing the resulting upper water-absorbing paper layer portion, the water-absorbing mixture layer portion, and the lower water-absorbing paper layer portion to integrally form them to produce an absorber, disposing the produced absorber on a water-impermeable film member, and, disposing a water-permeable layer part formed of a water-permeable porous member on the disposed absorber;

in addition, the present invention is a method of producing a sanitary article, comprising:

forming a lower water-absorbing paper layer portion formed of at least one sheet of water-absorbing paper, disposing a mixture containing a crushed pulp fiber material beaten to a fiber length of 0.1 to 7 mm, in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin in an amount less than the crushed pulp fiber material on the lower water-absorbing paper layer portion while aspirating from below the lower water-absorbing paper layer portion to form a water-absorbing mixture layer portion containing the crushed pulp fiber material, the crushed tea leaves, the crushed plastic-containing material, and the water-absorbing resin, disposing an upper water-absorbing paper layer portion formed of at least one sheet of water-absorbing paper on the water-absorbing mixture layer portion, pressing the resulting upper water-absorbing paper layer portion, the water-absorbing mixture layer portion, and the lower water-absorbing paper layer portion to integrally form them to produce an absorber, disposing the produced absorber on a water-impermeable film member, and, disposing a water-permeable layer part formed of a water-permeable porous member on the disposed absorber;

furthermore, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, laying a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a crushed pulp fiber material beaten to a fiber length of 0.1 to 7 mm, and the lower water-absorbing mixture layer portion is formed from a mixture containing a crushed pulp fiber material beaten to a fiber length of 0.1 to 7 mm, in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material;

still further, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a crushed pulp fiber material beaten to have a fiber length of 0.1 to 7 mm, and the lower water-absorbing mixture layer portion is formed from a mixture containing a crushed pulp fiber material beaten to a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin;

still additionally, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material;

in addition to these, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm and crushed tea leaves having a particle size of 0.05 to 4.6 mm in content percentage of not more than 1 weight % of fine particle with particle size of less than 0.05 mm, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin;

besides these, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a crushed plastic-containing material in an amount less than the crushed pulp fiber material, and the lower water-absorbing mixture layer portion is formed from a mixture containing a crushed pulp fiber material beaten to a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a water-absorbing resin in an amount less than the crushed pulp fiber material;

still besides these, the present invention is a method of producing a sanitary article, comprising:

disposing an absorbing material powder mixture on a lower water-absorbing paper layer portion formed of at least one sheet of water-absorbing paper while aspirating from below the lower water-absorbing paper layer portion to form a lower water-absorbing mixture layer portion, covering over the lower water-absorbing mixture layer portion with one or more sheet of thin paper to form an intermediate water-absorbing paper layer portion, disposing a water-absorbing material powder mixture on the intermediate water-absorbing paper layer portion while aspirating from below the lower water-absorbing paper layer portion to form an upper water-absorbing mixture layer portion, disposing an upper water-absorbing paper layer portion formed of at least one sheet of water-absorbing paper on the upper water-absorbing mixture layer portion to form a stratified material, press-shaping integrally the stratified material formed of the upper water-absorbing paper layer portion, the upper water-absorbing mixture layer portion, the intermediate water-absorbing paper layer portion, the lower water-absorbing mixture layer portion, and the lower water-absorbing paper layer portion to produce an absorber, disposing the produced absorber on a water-impermeable film member, and, disposing a water-permeable layer part formed of a water-permeable porous member on the disposed absorber to produce the sanitary article;

wherein the upper water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, and a crushed plastic-containing material in an amount less than the crushed pulp fiber material, and the lower water-absorbing mixture layer portion is formed from a mixture containing a crushed pulp fiber material beaten to have a fiber length of 0.1 to 7 mm in content percentage of not more than 5 weight % of fine particle with particle size of less than 0.1 mm, crushed tea leaves having a particle size of 0.05 to 4.6 mm in content percentage of not more than 1 weight % of fine particle with particle size of less than 0.05 mm, a crushed plastic-containing material in an amount less than the crushed pulp fiber material, and a water-absorbing resin.

In the absorber of the present invention, the crushed plastic-containing material encompasses crushed synthetic resin fiber, crushed biodegradable synthetic resin fiber, crushed waste synthetic resin fiber, crushed waste biodegradable synthetic resin fiber, crushed synthetic resin, crushed biodegradable synthetic resin, crushed waste synthetic resin, crushed waste biodegradable synthetic resin, crushed synthetic rubber, crushed biodegradable synthetic rubber, crushed waste synthetic rubber, crushed waste biodegradable synthetic rubber, crushed plastic film, crushed biodegradable plastic film, crushed waste plastic film, crushed waste biodegradable plastic film, crushed plastic-containing disposable diaper, crushed biodegradable plastic-containing disposable diaper, crushed waste plastic-containing disposable diaper, crushed waste biodegradable plastic-containing disposable diaper, crushed plastic-containing breast pad, crushed biodegradable plastic-containing breast pad, crushed waste plastic-containing breast pad, crushed waste biodegradable plastic-containing breast pad, crushed plastic-containing urine pad, crushed biodegradable plastic-containing urine pad, crushed waste plastic-containing urine pad, crushed waste biodegradable plastic-containing urine pad, crushed plastic-containing sanitary napkin, crushed biodegradable plastic-containing sanitary napkin, crushed waste plastic-containing sanitary napkin, crushed waste biodegradable plastic-containing sanitary napkin, crushed plastic nonwoven fabric, crushed biodegradable plastic nonwoven fabric, crushed waste plastic nonwoven fabric, crushed waste biodegradable plastic nonwoven fabric, crushed laminate paper, crushed biodegradable laminate paper, crushed waste laminate paper, crushed waste biodegradable laminate paper, or plastic-rich separated products through classifying these crushed products, or mixtures containing two or more thereof. In the absorber of the present invention, the water-absorbing resin includes water-absorbing resin, waste water-absorbing resin, highly water-absorbing resin, highly water-absorbing waste resin, beaten and crushed water-absorbing fiber, beaten and crushed waste water-absorbing fiber, or mixtures of crushed products of two or more thereof.

In the absorber of the present invention, the crushed tea leaves encompass crushed crude leaves of tea plant, crushed dry leaves of tea plant, crushed tea leaves of green tea, crushed tea leaves of oolong tea, crushed tea leaves of red tea, crushed tea dregs of green tea, crushed tea dregs of oolong tea, crushed tea dregs of red tea, or mixtures of two or more crushed products thereof. When a dry material of leach liquor of tea leaves is mixed, the dry material of leach liquor of tea leaves and/or tea dregs may be a leach liquor of tea leaves, that is, a leach liquor of crude leaves of tea plant, leach liquor of dry leaves of tea plant, leach liquor of tea leaves of green tea, leach liquor of tea leaves of oolong tea, leach liquor of tea leaves of red tea, leach liquor of tea dregs of green tea, leach liquor of tea dregs of oolong tea, leach liquor of tea dregs of red tea, or dry materials of mixtures of two or more leach liquors thereof.

Figure 1:
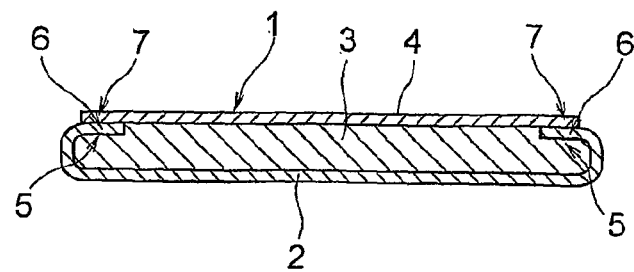
FIG. 1 is an illustrative view of an absorber of an Example according to the present invention.

EXPLANATIONS OF LETTERS OR NUMERALS 1, 8, 9: absorber;
2: lower water-absorbing paper layer portion;
3: water-absorbing mixture layer portion;
4: upper water-absorbing paper layer portion;
5: upper water-absorbing mixture layer portion of water-absorbing mixture layer portion 3;
6: marginal portion of lower water-absorbing paper layer portion 2;
7: marginal portion of back and forth and around of upper water-absorbing paper layer portion 4;
10: lower water-absorbing mixture layer portion;
11: intermediate water-absorbing paper layer portion;
12: upper water-absorbing mixture layer portion;
13: marginal portion of upper water-absorbing mixture layer portion 12;
14, 19, 20: sanitary article;
15: water-impermeable film portion;
16: water-permeable layer part;
17: marginal portion of back and forth and around of water-permeable layer part 16;
18: marginal portion of back and forth and around of water-impermeable film portion 15;
21: lower thin paper;
22: lower thin paper-supply roll;
23: lower thin paper-taking roller;
24: lower thin paper-laying site;
25: stacking machine for supplying water-absorbing material mixture;
26: supply roller;
27: laying site of water-absorbing material mixture;
28: supply hopper of water-absorbing material mixture;
29, 55, 66: aspiration box;
30: absorbing material mixture
31: folding machine of lower thin paper margin;
32: stack for sanitary article;
33: upper thin paper-laying site;
34: upper thin paper;
35: upper thin paper supply roll;
36: upper thin paper-taking roll;
37: embossing machine;
38: mat cutter;
39: polyethylene film for back film;
40: supply site of polyethylene film for back film 39;
41: polyethylene film supply roll;
42: polypropylene nonwoven fabric;
43: supply site of polypropylene nonwoven fabric 42;
44: roll for polypropylene nonwoven fabric 42;
45: sprayer for hot-melt adhesive;
46: side-seal machine;
47: second spreader for highly water-absorbing resin 8;
48: product cutter;
49: product-conveying path;
50: first water-absorbing mixture;
51: first stacking machine for supplying first water-absorbing mixture;
52: supply roller of first stacking machine 51;
53: site to lay first water-absorbing material mixture;
54: first water-absorbing material mixture-supplying hopper;
56, 67: pressing device;
57: intermediate thin paper;
58: intermediate thin paper laying site;
59: intermediate thin paper-supply roll;
60: intermediate thin paper-taking roller;
61: second water-absorbing material mixture;
62: second stacking machine for supplying second water-absorbing material mixture 61;
63: supply roller of second stacking machine;
64: second water-absorbing material mixture laying site;
65: second water-absorbing material mixture-supplying hopper;
68: spreading site of highly water-absorbing resin;
69: spreading device of highly water-absorbing resin

PREFERRED MODE FOR CARRYING OUT THE INVENTION

The absorber of the present invention can be used for sanitary articles such as auxiliary nursing-care mat, disposable diaper, disposable diaper for animals, sanitary napkin, sanitary napkin for animals, breast pad, sweat pad, urine pad, and sheet for animals as their absorbers, contains crushed tea leaves, and can maintain proper sanitary conditions for a long period of at least 48 hours after use, for example. The sanitary article of the present invention is formed by providing the absorber of the present invention containing crushed tea leaves between a water-permeable layer part to form an upper surface and a water-impermeable film portion to form a lower surface, can be made into auxiliary bedding sheet, auxiliary nursing-care mat, disposable diaper, disposable diaper for animals, sanitary napkin, sanitary napkin for animals, breast pad, sweat pad, urine pad, and sheet for animals, etc., and can maintain proper sanitary conditions for a long period of at least 48 hours after use, for example, since containing the crushed tea leaves.

In the present invention, the absorber includes the lower water-absorbing paper layer portion that is formed of one or more sheet of thin paper and forms the lower surface of the absorber, the water-absorbing mixture layer portion formed of the water-absorbing material mixture that contains the crushed pulp fiber material, the crushed tea leaves, and the water-absorbing resin in an amount less than the crushed pulp fiber material in layers, and the upper water-absorbing paper layer portion that covers over the water-absorbing mixture layer and is formed of one or more sheet of thin paper to form the upper surface of the absorber; the upper water-absorbing paper layer portion, the water-absorbing mixture layer portion, and the lower water-absorbing paper layer portion are mated and formed integrally by press-shaping to form the absorber. In the absorber of the present invention, the upper water-absorbing paper layer portion and the lower water-absorbing paper layer portion may be fixed by pressure bonding or adhering with an adhesive.

In the present invention, the absorber is formed as follows. As regards an one-layer type absorber, for example, a lower water-absorbing paper layer portion is formed from one or more sheet of thin paper by disposing one or more sheet of thin paper on a net conveyer of a conveying means. The water-absorbing material mixture containing the crushed pulp fiber material beaten to have a fiber length of 0.1 to 7 mm, the crushed tea leaves having a particle size of 0.05 to 4.6 mm, and the water-absorbing resin in an amount less than the crushed pulp fiber material is disposed in layers, a negative pressure is applied from under the net conveyer to aspirate them, the thickness of the disposed water-absorbing material mixture is entirely made uniform by the aspirating action, thereby forming the water-absorbing mixture layer portion containing the crushed pulp fiber material, the crushed tea leaves, and the water-absorbing resin. The resulting water-absorbing mixture layer portion is covered with one or more sheet of thin paper and the upper water-absorbing paper layer portion is formed from the one or more sheet of thin paper. The resulting upper water-absorbing paper layer portion, the water-absorbing material mixture layer part formed of the water-absorbing material mixture under it, and the lower water-absorbing paper layer portion under it form a stratified material; and the stratified material is pressed and shaped integrally to form the absorber.

In the present invention, the thin paper is water-absorbing paper with higher water-absorbing capability or liquid-absorbing paper with higher liquid-absorbing capability, forms the water-absorbing paper layer part in the absorber or sanitary articles using the absorber, and acts to absorb and impregnate water into the water-absorbing mixture layer portion under it. It is necessary in the present invention that the water-absorbing mixture layer portion is formed by moderately dispersing the crushed tea leaves into the crushed pulp fiber material in order to impart water-absorbing property, water-holding property, and odor-eliminating to the absorber. In the present invention, in order to moderately disperse the crushed tea leaves into the crushed pulp fiber material, the crushed pulp fiber material containing substantially no fine particles having a particle size of less than 0.1 mm and the crushed tea leaves containing substantially no fine particles having a particle size of less than 0.05 mm. It has been found that the properties of the absorber or sanitary articles using the absorber can be improved by mixing the crushed pulp fiber material containing substantially no fine particles and the crushed tea leaves containing substantially no fine particles.

It is preferred in the present invention that the crushed pulp fiber material beaten to have a fiber length of 0.1 to 7 mm is used as the crushed pulp fiber material of the raw material to form the water-absorbing mixture layer portion in order to hold the crushed tea leaves between the fiber particles and the crushed tea leaves as the raw material to form the water-absorbing mixture layer portion are prepared to have a particle size of 0.05 to 4.6 mm with substantially no fine particles so that the particles of the crushed tea leaves do not block the space between the crushed pulp fiber material particles. In the present invention, when the absorber is produced to have a larger infiltration velocity and a larger drying velocity, the mixing amount of the crushed tea leaves to form the water-absorbing mixture layer portion is 10% to 50% by weight based on the crushed pulp fiber material as dry weight, preferably 14% to 43% by weight based on the crushed pulp fiber material, more preferably 14% to 30% by weight based on the crushed pulp fiber material. In sanitary articles necessary to enhance the water-absorbing and odor-eliminating functions at the sacrifice of the infiltration and drying velocities such as auxiliary nursing-care mat and sheet for pets, the mixing amount of the crushed tea leaves in the water-absorbing mixture layer portion is 50% by weight or more based on the crushed pulp fiber material as dry weight, preferably 50% to 70% by weight based on the crushed pulp fiber material in particular. When the dry material of the leach liquor of tea-leaves is mixed into the water-absorbing mixture layer portion, it is preferred that 0.135 g or more of the dry material of the leach liquor of tea-leaves is mixed per 1 $m^2$ of the water-absorbing mixture layer portion, i.e. per 14 g.

In the present invention, the mixture of the crushed tea leaves can be prepared by mixing independently the crushed tea leaves with the crushed pulp fiber material disposed on water-absorbing paper or by disposing the mixture of the crushed tea leaves and the crushed pulp fiber material on water-absorbing paper. That is, the method may be carried out by disposing the mixture of the crushed pulp fiber material, the crushed tea leaves, and the water-absorbing resin or by spreading the crushed pulp fiber material over the mixture of the crushed pulp fiber material and the water-absorbing resin. Any one of the methods to carry out the mixing of the crushed tea leaves is preferable since medium-coarse or large-coarse crushed tea leaves are easily mixed when mixing the crushed tea leaves.

However, as regards the mixing amount of the crushed tea leaves, when the crushed tea leaves are mixed with the crushed pulp fiber material in a mixing rate of 55% by weight or more of the crushed tea leaves, the water-absorbing performances of sheets such as infiltration velocity, drying velocity, return sheet number, spot property, and return amount with respect to water-absorbing properties degrade in general as for all of fine-coarse, medium-coarse, and large-coarse crushed tea leaves. However, it has been found that the water-absorbing performances are not significantly different from those not mixed with the crushed tea leaves when the mixing amount of the crushed tea leaves in the water-absorbing mixture layer portion is 14% to 43% by weight as dry weight based on the crushed pulp fiber material, preferably 14% to 30% by weight.

In the absorber of the present invention, the crushed tea leaves are mixed into the water-absorbing mixture layer portion in order to inhibit microorganism proliferation and to eliminate odor after use. However, the coloring due to the particles of crushed tea leaves at the surface of the absorber or sanitary articles using the absorber comes to out-of-sight from outside and the appearance can be improved when the mixing of the particles of crushed tea leaves is carried out so that the amount of the particles of crushed tea leaves is less at the surface area of the water-absorbing mixture layer portion and the particles are distributed inside as much as possible in the process to produce the water-absorbing mixture layer portion.

In the present invention, the particles of crushed tea leaves are prepared to have a particle size less than that of the crushed pulp fiber material, aspiration is applied by a negative pressure from below the water-absorbing paper on which the crushed pulp fiber material or the mixture of the crushed pulp fiber material and the water-absorbing resin mixed with the particles of crushed tea leaves is disposed, furthermore, the specific gravity of the particles of crushed tea leaves is larger than those of the crushed pulp fiber material and the water-absorbing resin, therefore, the particles of crushed tea leaves mixed with the crushed pulp fiber material or the mixture of the crushed pulp fiber material and the water-absorbing resin can move downward between the particles of the pulp fiber material and be distributed so that the content increases from upper to lower within the water-absorbing mixture layer portion formed from the crushed pulp fiber material, the crushed tea leaves, and the water-absorbing resin. In the water-absorbing mixture layer portion, the particles of crushed tea leaves are supported mainly between the fiber particles of the crushed pulp fiber material within the layer of the water-absorbing mixture layer portion formed of the water-absorbing material of the crushed pulp fiber material, the crushed tea leaves, and the water-absorbing resin disposed and formed on the lower water-absorbing paper layer portion.

Accordingly, in the present invention, the crushed tea leaves are distributed within the water-absorbing mixture layer portion mainly downward thereof, only a little amount of the crushed tea leaves remains at the surface of the water-absorbing mixture layer portion, moreover, its upside is covered with the upper paper layer part, therefore, the surface of the water-absorbing mixture layer portion is formed as good-looking.

In the present invention, mixing of the crushed tea leaves with the crushed pulp fiber material or the mixture of the crushed pulp fiber material and the water-absorbing resin can be carried out by spreading the crushed tea leaves from upside onto the crushed pulp fiber material or onto the mixture of the crushed pulp fiber material and the water-absorbing resin and moving downward and dispersing within the crushed pulp fiber material or within the mixture of the crushed pulp fiber material and the water-absorbing resin.

In addition, in the present invention, the water-absorbing resin is a relatively fine powder, and the dispersion is carried out simultaneously with the dispersion of the crushed tea leaves within the water-absorbing mixture layer portion. The dispersion of the water-absorbing resin can also be carried out by dispersing the water-absorbing resin from upside onto the crushed pulp fiber material or onto the mixture of the crushed pulp fiber material and the water-absorbing resin. In this case, the water-absorbing resin is mixed through moving downward and dispersing within the crushed pulp fiber material or within the water-absorbing material mixture similarly as the mixing of the crushed tea leaves.

In the present invention, the water-absorbing mixture layer portion is formed by disposing a mixture containing the crushed pulp fiber material beaten to have a fiber length of 0.1 to 7 mm, the crushed tea leaves having a particle size of 0.05 to 4.6 mm, and the water-absorbing resin in an amount less than the crushed pulp fiber material on the lower water-absorbing paper layer portion by aspiration from downside into a mixture layer as a uniform-thickness layer. The water-absorbing mixture layer portion may also be formed in another way by spreading the crushed tea leaves having a particle size of 0.05 to 4.6 mm and/or the water-absorbing resin onto the disposed crushed pulp fiber material beaten to have a fiber length of 0.1 to 7 mm and dispersing the spread crushed tea leaves or the water-absorbing resin into the crushed pulp fiber material.

In the present invention, the marginal portion of the lower water-absorbing paper layer portion is folded on the marginal portion of the water-absorbing mixture layer portion formed on the lower water-absorbing paper layer portion as described above, the marginal portion of the water-absorbing mixture layer portion is pressed by the marginal portion of the lower water-absorbing paper layer portion, then the upper water-absorbing paper layer portion is mounted on the water-absorbing mixture layer portion on which the marginal portion of the lower water-absorbing paper layer portion is folded, the water-absorbing mixture layer portion is formed between the upper water-absorbing paper layer portion and the lower water-absorbing paper layer portion to form the stratified material, and the stratified material is press-shaped by embossing treatment, thereby the absorber is formed. In the absorber, the water-absorbing mixture layer portion is integrally formed between the upper water-absorbing mixture layer portion and the lower water-absorbing mixture layer portion through pressure-bonding the upper water-absorbing mixture layer portion and the lower water-absorbing mixture layer portion. When the embossing treatment is carried out, the marginal portion of the upper water-absorbing paper layer portion and the marginal portion of the lower water-absorbing paper layer portion are pressure-bonded each other, or adhered or stuck through an adhesive or a tackiness agent to be fixed or attached to be not easily separable, thereby the absorber may be formed.

As regards the absorber mixed with the crushed tea leaves in the present invention, preferably, the smaller is the particle size of the particles of the crushed tea leaves and the higher is the odor-eliminating property. However, it has been found that the smaller particle size of the crushed tea leaves brings about decrease of the infiltration rate, drying velocity, and water-absorbing amount of the absorber with water and liquid and the spot property degrades. Therefore, in the present invention, the content of fine particles of the crushed tea leaves and the crushed pulp fiber material to result in the degradation of the water-absorbing performance of the absorber is reduced as low as possible. However, the crushed pulp fiber material has a higher infiltration velocity to water and liquid in contrast to the crushed tea leaves, it is therefore preferred that the content of the fine particles of the crushed pulp fiber material beaten to have a fiber length of below 0.1 mm is adjusted 5% by weight or less, preferably 3% by weight or less. It is also preferred as for the crushed tea leaves that the content of the fine particles of the crushed tea leaves having a particle of below 0.05 mm is 1% by weight or less. In this connection, the absorber and sanitary articles using the sanitary article can have the odor-eliminating property after use and maintain a relatively high infiltration velocity, drying velocity, and water-absorbing amount to liquid such as urine by preparing substantially not to get mixed in the fine particles of the crushed tea leaves having a particle of below 0.05 mm.

In the present invention, the paper layer part of the absorber may be formed as three layers of the upper water-absorbing paper layer portion, the intermediate water-absorbing paper layer portion, and the upper water-absorbing paper layer portion; the upper water-absorbing mixture layer portion may be formed between the upper water-absorbing paper layer portion and the intermediate water-absorbing paper layer portion, and the lower water-absorbing mixture layer portion may be formed between the intermediate water-absorbing paper layer portion and the lower water-absorbing paper layer portion, respectively, thereby the water-absorbing mixture layer portion may be provided as two layers. When the water-absorbing paper layer part is provided as three layers and the water-absorbing mixture layer portion is provided as two layers as described above, the absorber absorbs water at each of the three layers of the water-absorbing paper layer part and also absorbs and retains water at each of the two layers of the upper water-absorbing mixture layer portion and the lower water-absorbing mixture layer portion, therefore, the water-absorbing performance of the absorber can be improved, the infiltration velocity and the drying velocity to liquid such as voided urine can be increased, and the spot property can be decreased compared to the case of one layer. Even as regards the absorber provided with two layers of the water-absorbing mixture layer portion, the infiltration velocity and the drying velocity can be increased and the spot property can be decreased when the part of lower particle sizes of the crushed tea leaves is excluded from mixing into the water-absorbing mixture layer portion. Essentially, the paper layer part can be formed into still more layers and the water-absorbing mixture layer portion can be formed into three or more layers, for example.

In the absorber of the present invention, the water-absorbing mixture layer portion is formed by disposing the water-absorbing material mixture containing the crushed pulp fiber material having a fiber length of 0.1 to 7 mm, the crushed tea leaves having a particle size of 0.05 to 4.6 mm, and the water-absorbing resin in an amount less than the crushed pulp fiber material on the water-absorbing paper layer part, and distributing the fine crushed material particles of each of the crushed pulp fiber material, the crushed tea leaves, and the water-absorbing resin so that the fine crushed material particles come to rich from the upper face part to downward by aspirating from below the water-absorbing paper layer part; therefore, the infiltration velocity and the drying velocity can be increased and the spot property can be decreased and the odor-eliminating performance can be improved for bodily wastes. The present invention is based on the discovery of the fact in the water-absorbing mixture layer portion. Moreover, the crushed tea leaves are distributed to increase the concentration from the upper face part to downward in the water-absorbing mixture layer portion; it is therefore preferred for its appearance since the dirty impression due to mixing the crushed tea leaves is relieved.

When the water-absorbing resin absorbs water, the resin swells to disturb the infiltration of urine, etc., it is therefore preferred in the present invention that the mixing of the water-absorbing resin is carried out only at the lower water-absorbing mixture layer portion in the absorber that is provided with two layers of the water-absorbing mixture layer portion by providing the intermediate paper layer part. In this connection, the amount of the water-absorbing resin in the lower water-absorbing mixture layer portion can be much more than the amount of the water-absorbing resin in the upper water-absorbing mixture layer portion. When the content of the water-absorbing resin is increased at the lower water-absorbing mixture layer portion as described above, the moisture that infiltrates and accumulates at the water-impermeable film portion can be reduced as low as possible in sheets, etc. and the return amount of voided urine, etc. can be reduced.

In the absorber of the present invention, the amount of the crushed tea leaves to the amount of the crushed pulp fiber material in the water-absorbing mixture layer portion and the upper or lower water-absorbing mixture layer portion is 10 to 100 parts by weight of the crushed tea leaves to 70 parts by weight of the crushed pulp fiber material, for example; the amount of the crushed tea leaves mixed with the crushed pulp fiber material of 10 parts by weight or less is not preferable since the odor-eliminating action and bacterial growth-inhibitory action by the crushed tea leaves are insufficient, and the amount of the crushed tea leaves mixed into the water-absorbing mixture layer portion of above 60% by weight is not preferable for the absorber and sanitary articles using the sanitary article since the infiltration velocity, the drying velocity, and the water-absorbing performance degrade as for the absorber and sanitary articles using the sanitary article.

In the present invention, the paper layer part may be formed by overlapping one or more sheet of sanitary paper such as tissue paper, waste tissue paper, and toilet paper or thin paper such as sanitary thin paper. It is necessary in the water-absorbing mixture layer portion of the absorber or the sanitary article of the present invention that the particles of the crushed tea leaves and the particles of the water-absorbing resin are sustained between the particles of the crushed pulp fiber material. In order to sustain stably the particles of the crushed tea leaves between the crushed pulp fiber material in the present invention, the particle size of the crushed pulp fiber material is adjusted to 0.1 to 7 mm, preferably 0.3 to 5 mm, and the particle size of the crushed tea leaves is adjusted to 0.05 to 4.6 mm, preferably 0.7 to 3.8 mm. When the particle size of the crushed tea leaves is 4.6 mm or larger, there may arise a problem of mixture non-uniformity that the crushed tea leaves remain at the upper part of the layer of the crushed pulp fiber material even being dispersed and the amount mixed into the layer of the crushed pulp fiber material is less even being aspirated from downside by a pump. In addition, the finer particle size of 0.05 mm or less of the crushed tea leaves is not preferable since the water-absorbing performance degrades and also mixture non-uniformity occurs such that the particles of the crushed tea leaves pass through the water-absorbing mixture layer portion and the amount of the particles of the crushed tea leaves remained within the water-absorbing mixture layer portion decreases.

The finer particle size of the crushed tea leaves is not preferable for sanitary articles in particular since the particles accumulate downward in use, or float on excrement such as urine and migrate upward to display a dirty appearance. From the viewpoint of less mixture non-uniformity and proper water-absorbing performance, the particle size of the crushed tea leaves is preferably 0.05 to 4.6 mm, more preferably 0.7 to 3.8 mm. The crushed tea leaves of particle size of 0.05 to 4.6 mm can be classified and used as fine-coarse crushed tea leaves of particle size of 0.05 to 0.6 mm, medium-coarse crushed tea leaves of particle size of 0.7 to 2.4 mm, and large-coarse crushed tea leaves of particle size of 2.1 to 4.6 mm based on their particle size, for example, thereby the absorbing property of the absorber and sanitary articles using the sanitary article can be improved. It is preferred in particular that the absorber and sanitary articles using the sanitary article, into which the medium-coarse crushed tea leaves of particle size of 0.7 to 2.4 mm and the large-coarse crushed tea leaves of particle size of 2.1 to 4.6 mm are dispersed, can improve the absorbing property of liquid such as urine, for example, the infiltration velocity, drying velocity, return sheet number, and spot property. In the present invention, the lower limit of the particle size with respect to the range of particle size of the crushed materials means that the content of particles having a particle size lower than this lower limit is 1% by weight or less.

And, in the absorber of the present invention, the water-absorbing mixture layer portion containing the crushed pulp fiber material beaten to have a fiber length of 0.1 to 7 mm, the crushed tea leaves having a particle size of 0.05 to 4.6 mm, and the water-absorbing resin in an amount less than the crushed pulp fiber material can be formed by disposing the mixture of the crushed pulp fiber material beaten to have a fiber length of 0.1 to 7 mm and the water-absorbing resin in an amount less than the crushed pulp fiber material, spreading the crushed tea leaves having a particle size of 0.05 to 4.6 mm onto the disposed mixture containing the crushed pulp fiber material and the water-absorbing resin while aspirating from below the disposed mixture, and dispersing the spread crushed tea leaves into the disposed mixture of the crushed pulp fiber material and the water-absorbing resin.

Furthermore, in the absorber of the present invention, the water-absorbing mixture layer portion containing the crushed pulp fiber material beaten to have a fiber length of 0.1 to 7 mm, the crushed tea leaves having a particle size of 0.05 to 4.6 mm, the crushed plastic-containing material in an amount less than the crushed pulp fiber material, and the water-absorbing resin can be formed by disposing the mixture of the crushed pulp fiber material beaten to have a fiber length of 0.1 to 7 mm, the crushed plastic-containing material in an amount less than the crushed pulp fiber material, and the water-absorbing resin, spreading the crushed tea leaves having a particle size of 0.05 to 4.6 mm onto the disposed mixture containing the crushed pulp fiber material, the crushed plastic-containing material, and the water-absorbing resin while aspirating from below the disposed mixture, and dispersing the spread crushed tea leaves into the disposed mixture of the crushed pulp fiber material, the crushed plastic-containing material, and the water-absorbing resin.

And, in the absorber of the present invention, the water-absorbing mixture layer portion containing the crushed pulp fiber material beaten to have a fiber length of 0.1 to 7 mm, the crushed tea leaves having a particle size of 0.05 to 4.6 mm, and the water-absorbing resin in an amount less than the crushed pulp fiber material can be formed by disposing the mixture of the crushed pulp fiber material beaten to have a fiber length of 0.1 to 7 mm, the crushed tea leaves having a particle size of 0.05 to 4.6 mm, and the water-absorbing resin in an amount less than the crushed pulp fiber material, and dispersing the crushed tea leaves and the water-absorbing resin into the layer of the crushed pulp fiber material beaten to have a fiber length of 0.1 to 7 mm by aspirating from below the disposed mixture containing the crushed pulp fiber material, the crushed tea leaves, and the water-absorbing resin.

Furthermore, in the absorber of the present invention, the water-absorbing mixture layer portion containing the crushed pulp fiber material beaten to have a fiber length of 0.1 to 7 mm, the crushed tea leaves having a particle size of 0.05 to 4.6 mm, the crushed plastic-containing material in an amount less than the crushed pulp fiber material, and the water-absorbing resin can be formed by disposing the mixture containing the crushed pulp fiber material beaten to have a fiber length of 0.1 to 7 mm, the crushed tea leaves, the crushed plastic-containing material in an amount less than the crushed pulp fiber material, and the water-absorbing resin, dispersing the crushed tea leaves and the water-absorbing resin in the mixture into the layer of the disposed mixture of the crushed pulp fiber material and the crushed plastic-containing material by aspirating using a negative pressure from downside of the layer of the disposed mixture containing the crushed pulp fiber material, the crushed tea leaves, the crushed plastic-containing material, and the water-absorbing resin.

The crushed pulp fiber material used for the absorber of the present invention, sanitary articles using the absorber, and the production methods thereof is employed to impart cushion, water-absorbing, and water-holding properties to the absorber and sanitary articles using the absorber; the crushed pulp fiber material is exemplified by crushed toilet paper, crushed waste toilet paper, crushed tissue paper, crushed waste tissue paper, crushed decorative paper, crushed waste decorative paper, crushed tissue, crushed waste tissue, crushed paper cotton, crushed waste paper cotton, crushed paper towel, crushed waste paper towel, waste lavatory seat, waste toilet seat, puff powder, crushed disposable diaper, crushed waste disposable diaper, pulp-rich classified crushed waste disposable diaper, crushed sanitary napkin, crushed waste product of sanitary napkin, pulp-rich classified crushed waste product of sanitary napkin, crushed waste breast pad, crushed waste mamma pad, pulp-rich classified crushed waste breast pad, crushed urine pad, crushed waste urine pad, pulp-rich classified crushed urine pad, crushed wood pulp, crushed waste wood pulp, crushed used paper pulp, paper powder, crushed scrap paper, crushed scrap cardboard, crushed nonwoven fabric, crushed waste nonwoven fabric, crushed papermaking pulp, crushed waste papermaking pulp, crushed mechanical pulp, crushed waste mechanical pulp, crushed chemical pulp, crushed waste chemical pulp, crushed semi-chemical pulp, crushed waste semi-chemical pulp, crushed flocculent pulp, crushed waste flocculent pulp, crushed wooden pulp, crushed waste wooden pulp, crushed waste used paper pulp, crushed waste sanitary articles, classified fluff pulp of crushed waste sanitary articles, crushed water-absorbing fiber, crushed waste water-absorbing fiber, crushed water-absorbing resin, water absorbing resin-containing paper powder, paper powder generating at bookbinding, paper powder generating at nonwoven fabric production, paper powder generating at paper production, or paper powder generating at sanitary article production, and mixtures of two or more thereof.

Furthermore, in the absorber of the present invention, sanitary articles using the absorber, and the production methods thereof, the crushed pulp fiber material is used to impart cushion, water-absorbing, and water-holding properties to the absorber and sanitary articles, and encompasses crushed pulp fiber waste material. The crushed pulp fiber waste material is exemplified by crushed waste diaper or pulp-rich classified product thereof, crushed waste sanitary napkin or pulp-rich classified product thereof, crushed waste breast pad or pulp-rich classified product thereof, crushed waste urine pad or pulp-rich classified product thereof, crushed beaten wood pulp, crushed beaten used pulp, beaten wood powder, beaten paper powder, beaten punch dreg, crushed dreg paper, and mixtures of two or more thereof.

Furthermore, in the absorber of the present invention, sanitary articles using the absorber, and the production methods thereof, the crushed plastic-containing material is used for enhancing cushion and water-holding properties of the absorber and sanitary articles using the absorber; preferably, the plastic-containing material is a film-, sheet-, or braid-shape plastic-containing material or a biodegradable plastic-containing material having a particle size of 5 mm or less and a thickness of 2 mm or less, or mixtures of two or more plastic-containing materials as described above. Consequently, the absorber can be produced with a thickness of 5 mm or less; the plastic-containing material is exemplified by crushed synthetic resin fiber, crushed waste synthetic resin fiber, crushed synthetic resin, crushed waste synthetic resin, crushed synthetic rubber, crushed waste synthetic rubber, crushed plastic film, crushed waste plastic film, crushed biodegradable plastic film, crushed waste biodegradable plastic film, crushed disposable diaper, crushed waste disposable diaper, crushed breast pad, crushed waste breast pad, crushed urine pad, crushed waste urine pad, crushed sanitary napkin, crushed waste sanitary napkin, crushed plastic nonwoven fabric, crushed waste plastic nonwoven fabric, crushed biodegradable plastic nonwoven fabric, crushed waste biodegradable plastic nonwoven fabric, crushed laminate paper, crushed waste laminate paper, plastic crushed and separated by classification etc., biodegradable plastic-rich separated product, and mixtures of two or more thereof.

Still further, in the absorber of the present invention, sanitary articles using the absorber, and the production methods thereof, the water-absorbing resin is used for enhancing water-absorbing and water-holding properties of the absorber and sanitary articles using the absorber; the water-absorbing resin encompasses water-absorbing resin inadequate for highly water-absorbing resin, water-absorbing resin with lower ware-absorbing performance, waste water-absorbing resin thereof, highly water-absorbing resin, waste highly water-absorbing resin, beaten and crushed product of water-absorbing fiber, crushed waste product of water-absorbing fiber, and mixtures of two or more crushed products thereof.

Still additionally, in the absorber of the present invention, sanitary articles using the absorber, and the production methods thereof, the crushed tea leaves are used to impart bactericidal action and odor-eliminating action to the absorber and sanitary articles using the absorber; the crushed tea leaves are exemplified by crushed crude leaves of tea plant, crushed dry leaves of tea plant, dried or undried crushed tea leaves of green tea, dried or undried crushed tea leaves of oolong tea, dried or undried crushed tea leaves of red tea, dried or undried crushed tea dregs of green tea, dried or undried crushed tea dregs of oolong tea, dried or undried crushed tea dregs of red tea, and mixtures of two or more thereof. Still further, in the absorber of the present invention, sanitary articles using the absorber, and the production methods thereof, the tea leaves to form the crushed tea leaves encompass the dried or undried tea leaves and may be dried or undried crushed tea leaves of green tea, dried or undried crushed tea dregs of green tea, dried or undried crushed tea leaves of oolong tea, dried or undried crushed tea dregs of oolong tea, dried or undried crushed tea leaves of red tea, dried or undried crushed tea dregs of red tea, or mixtures of two or more tea leaves and/or tea dregs thereof.

Furthermore, in the absorber of the present invention, sanitary articles using the absorber, and the production methods thereof, the thin paper is provided in order to enhance the water-absorbing property to body fluid such as water and urine of the absorber and sanitary articles using the absorber and also to support the water-absorbing materials of the absorber and sanitary articles using the absorber, and the thin paper encompasses absorbable paper, thin paper, sanitary paper, sanitary thin paper, and decorative paper. In the present invention, one or more sheet of the thin paper is overlapped and pressure-bonded or at least a part thereof is adhered to form a water-absorbing paper layer part, upper and lower water-absorbing paper layer portion, and an intermediate water-absorbing paper layer portion.

In the sanitary article of the present invention and the production methods thereof, the water-permeable layer part is provided in order to protect the upper water-absorbing paper layer portion in use and to permit the passage of body fluid such as water and urine into the underlying water-absorbing mixture layer portion; the water-permeable layer part may be formed in sanitary articles from nonwoven fabric made of plastic fiber, waste plastic fiber, rayon fiber, waste rayon fiber, pulp fiber, waste pulp fiber, polyamide fiber, waste polyamide fiber, polyester fiber, waste polyester fiber, biodegradable plastic fiber such as polylactate, waste biodegradable plastic fiber, or nonwoven fabric made of two or more of these fibers or waste fibers.

Furthermore, in the absorber of the present invention, sanitary articles using the absorber, and the production methods thereof, the water-impermeable film portion is provided in order to reserve the urine, which has been excreted in a relatively large amount and cannot be absorbed into the water-absorbing mixture layer portion etc. in use, and to prevent it from flowing outside. The water-impermeable film portion has a hardly breakable property and a foldable flexibility and may be formed from film-shape or thin sheet-shape plastic film material or biodegradable plastic film material. The plastic film material is exemplified by polyethylene film and polypropylene film. The other plastic film materials are exemplified by polyvinyl chloride, polystyrene,polyvinylidene chloride, polyester, nylon, and polyvinyl alcohol. The biodegradable plastic film material is exemplified by polycaprolactone, polybutylene succinate, polyethylene succinate, polybutylene succinate adipate, and polybutylene succinate carbonate.

In the present invention, the terms of "infiltration velocity", "drying velocity", "spot property", "return amount", "return sheet number", and "water-absorbing amount" to express the water-absorbing performance of the "absorber" and "sanitary article" in particular of "sanitary article" such as disposable diaper are explained in the following.

The "infiltration velocity" of sanitary articles in the present invention is measured as to the period (second) from the time when 25 cc of normal saline solution of 0.9% by weight is poured to one point of central portion of a sheet until the time when a star-shape wet pattern at the poured portion spreads over the entire sheet and is expressed by the interval of the times.

The "drying velocity" of sanitary articles in the present invention is measured as to the period (second) from the time when 25 cc of normal saline solution of 0.9% by weight is poured to one point of central portion of a sheet until the time when the poured surface comes to dry state sensed from finger feeling and is expressed by the interval of the times(second).

The "spot property" of sanitary articles in the present invention is measured as to longitudinal and traverse sizes of the wetted portion after measuring the drying velocity and is expressed by the half value of the sum of the longitudinal and traverse sizes: [(longitudinal size+traverse size)×½].

The "return amount" of sanitary articles in the present invention is obtained by pouring 25 cc of normal saline solution of 0.9% by weight to one point of central portion of a sheet, allowing to stand for 3 minutes, laying 10 sheets of circular filter paper of diameter 110 mm on the poured site and disposing a weight of 1.5 kg thereon, and measuring the amount of water absorbed by the filter paper after allowing to stand for 1 minute and is expressed by the measured amount of water. In addition, the "return sheet number" indicates the sheet number of wet filter paper determined by measuring the sheet number of filter paper that has absorbed water and is under wet state sensed from finger feeling when measuring the return amount.

The "water-absorbing amount" of sanitary articles in the present invention is obtained by charging tap water into a measurement vessel at 20° C., immersing perfectly a sanitary article into the tap water to allow to stand for 3 minutes, followed by taking out and hanging it for 5 minutes amount of water absorbed by the hanged sanitary article and is expressed by the measured weight of water.

The "infiltration velocity", "water-absorbing amount", and "drying velocity" are important with respect to sanitary articles having one layer-type water-absorbing mixture layer portion, in particular with respect to "disposable diaper", "urine pad", and "absorber"; and larger "infiltration velocity", much "water-absorbing amount", and larger "drying velocity" are desired. However, "infiltration velocity" and "drying velocity" are said to be important with respect to "pet sheet" and "auxiliary nursing—care mat". The odor-elimination or odor-removal by virtue of the crushed tea leaves is important for all of "disposable diaper", "urine pad", "absorber", "pet sheet", and "auxiliary nursing—care mat". In cases of odor-elimination or odor-removal for "disposable diaper", "urine pad", and "absorber", the crushed tea leaves may be medium-coarse, large-coarse, or mixture of medium-coarse and large-coarse, and the mixing amount of the tea leaves is 8 to 25 g/m². On the other hand, "infiltration velocity", "drying velocity", and "spot property" are important for the "pet sheet" and "auxiliary nursing—care mat"; in this connection, fine-coarse crushed tea leaves may lead to proper result in a range of 5 to 10 g/m², and medium-coarse and large-coarse crushed tea leaves may lead to proper result even in a range of 8 to 25 g/m².

The "infiltration velocity", "drying velocity, "spot property", "return sheet number", and "water-absorbing amount" with respect to the "water-absorbing performance" of the "thin regular-type pet sheet" were examined while changing the mixing amount of crushed tea leaves as regards the pet sheet having a water-absorbing mixture layer portion containing the crushed tea leaves with an outer size of width 300 mm by length 450 mm, an inner size of width 300 mm by length 400 mm, fluff pulp 7 g, and highly water-absorbing resin 3 g.

As a result, "infiltration velocity", "drying velocity", and "return sheet number" tend to decrease along with the increase of the mixing amount of the fine-coarse mixture in all of the cases where fine-coarse crushed tea leaves (hereinafter referred to as fine-coarse mixture) are mixed, where medium-coarse crushed tea leaves (hereinafter referred to as medium-coarse mixture) are mixed, and where large-coarse crushed tea leaves (hereinafter referred to as large-coarse mixture) are mixed. However, the "spot property" and "water-absorbing amount" tend to decrease along with the increase of the mixing amount of the fine-coarse mixture.

The "infiltration velocity", "drying velocity, "spot property", "return sheet number", and "water-absorbing amount" with respect to the "water-absorbing performance" of the "thin regular-type pet sheet" were examined while changing the particle size and mixing amount of crushed tea leaves to be mixed.

(1) Infiltration Velocity

When the mixing amount of tea leaves was 1 g, the infiltration velocity was the highest in the medium-coarse mixture, secondly high in the large-coarse mixture, and the lowest in the fine-coarse mixture. When the mixing amount of tea leaves was 3 g, the infiltration velocity was the highest in the fine-coarse mixture, secondly high in the large-coarse mixture, and the lowest in the medium-coarse mixture. When the mixing amount of tea leaves was 5 g, the infiltration velocity was the highest in the large-coarse mixture, secondly high in the fine-coarse mixture, and the lowest in the medium-coarse mixture. When the mixing amount of tea leaves was 7 g, the infiltration velocity was the highest in the fine-coarse mixture, secondly high in the large-coarse mixture, and the lowest in the medium-coarse mixture. When the mixing amount of tea leaves was 10 g, the infiltration velocity was the highest in the medium-coarse mixture, secondly high in the large-coarse mixture, and the lowest in the fine-coarse mixture.

(2) Drying Velocity

When the mixing amount of tea leaves was 1 g, the drying velocity was the highest in the large-coarse mixture, secondly high in the fine-coarse mixture, and the lowest in the medium-coarse mixture. When the mixing amount of tea leaves was 3 g, the drying velocity was the highest in the large-coarse mixture, secondly high in the medium-coarse mixture, and the lowest in the fine-coarse mixture. When the mixing amount of tea leaves was 5 g, the drying velocity was the highest in the large-coarse mixture, secondly high in the fine-coarse mixture, and the lowest in the medium-coarse mixture. When the mixing amount of tea leaves was 7 g, the drying velocity was the highest in the large-coarse mixture, secondly high in the medium-coarse mixture, and the lowest in the fine-coarse mixture. When the mixing amount of tea leaves was 10 g, the drying velocity was the highest in the medium-coarse mixture, secondly high in the large-coarse mixture, and the lowest in the fine-coarse mixture.

(3) Return Sheet Number

When the mixing amount of tea leaves was 1 g, the return sheet number was the highest in the large-coarse mixture, secondly high in the medium-coarse mixture, and the lowest in the fine-coarse mixture. When the mixing amount of tea leaves was 3 g, the return sheet number was the highest in the large-coarse mixture, secondly high in the medium-coarse mixture, and the lowest in the fine-coarse mixture. When the mixing amount of tea leaves was 5 g, the return sheet number was the highest in the fine-coarse mixture, secondly high in the medium-coarse mixture, and the lowest in the large-coarse mixture. When the mixing amount of tea leaves was 7 g, the return sheet number was the highest in the medium-coarse mixture, secondly high in the fine-coarse mixture, and the lowest in the large-coarse mixture. When the mixing amount of tea leaves was 10 g, the return sheet number was the highest in the medium-coarse mixture, secondly high in the large-coarse mixture, and the lowest in the fine-coarse mixture.

(4) Return Amount

When the mixing amount of tea leaves was 1 g, the return amount was the highest in the medium-coarse mixture, secondly high in the medium-coarse mixture, and the lowest in the fine-coarse mixture. When the mixing amount of tea leaves was 3 g, the return amount was the highest in the medium-coarse mixture, secondly high in the large-coarse mixture, and the lowest in the fine-coarse mixture. When the mixing amount of tea leaves was 5 g, the return amount was the highest in the fine-coarse mixture, secondly high in the medium-coarse mixture, and the lowest in the large-coarse mixture. When the mixing amount of tea leaves was 7 g, the return amount was the highest in the medium-coarse mixture, secondly high in the large-coarse mixture, and the lowest in the fine-coarse mixture. When the mixing amount of tea leaves was 10 g, the return amount was the highest in the medium-coarse mixture, secondly high in the large-coarse mixture, and the lowest in the fine-coarse mixture.

(5) Spot Property

When the mixing amount of tea leaves was 1 g, the spot property was the highest in the fine-coarse mixture, secondly high in the medium-coarse mixture, and the lowest in the large-coarse mixture. When the mixing amount of tea leaves was 3 g, the spot property was the highest in the large-coarse mixture, secondly high in the fine-coarse mixture, and the lowest in the medium-coarse mixture. When the mixing amount of tea leaves was 5 g, the spot property was the highest in the fine-coarse mixture, secondly high in the large-coarse mixture, and the lowest in the medium-coarse mixture. When the mixing amount of tea leaves was 7 g, spot property was the highest in the medium-coarse mixture, secondly high in the large-coarse mixture, and the lowest in the fine-coarse mixture. When the mixing amount of tea leaves was 10 g, the spot property was the highest in the fine-coarse mixture, secondly high in the large-coarse mixture, and the lowest in the medium-coarse mixture.

In cases of disposable diaper, urine pad, pet sheet, and sanitary napkin with the water-absorbing mixture layer portion of one-layer type, the particle size of the crushed tea leaves is preferably a medium-coarse mixture, more preferably a large-coarse mixture. In cases of disposable diaper, urine pad, pet sheet, and sanitary napkin with the water-absorbing mixture layer portion of two-layer type, when the upper and lower layers contain the same crushed tea leaves, the particle size of the crushed tea leaves is preferably a medium-coarse mixture, more preferably a large-coarse mixture; when the upper and lower layers are different in particle size, it is preferred that the upper water-absorbing mixture layer portion is of large-coarse mixture and the lower water-absorbing mixture layer portion is of large-coarse mixture.

Embodiments of the present invention are explained with respect to examples in the following, but the present invention should not be limited by the following explanations and illustrations.

Figure 2:
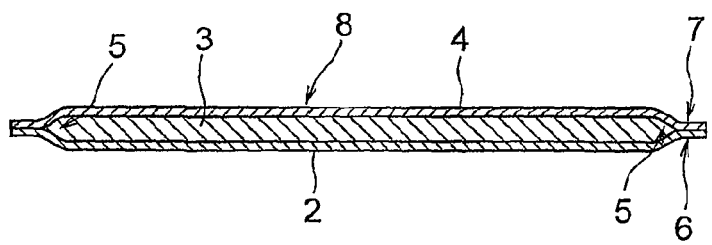
FIG. 2 is an illustrative view of an absorber of another Example according to the present invention different from the Example shown in FIG. 1.
Figure 3:
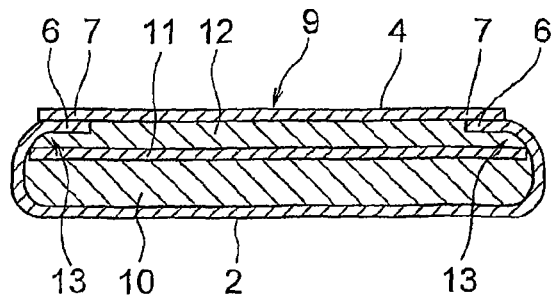
FIG. 3 is an illustrative view of an absorber of still another Example according to the present invention different from the Examples shown in FIGS. 1 and 2.
Figure 4:
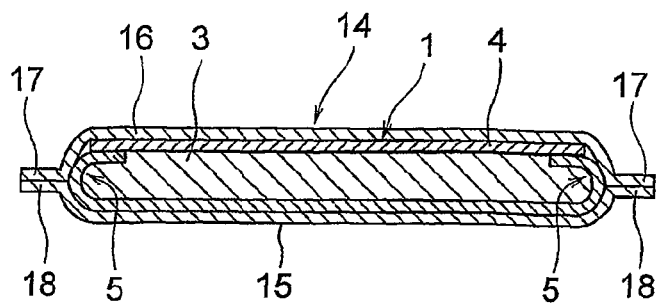
FIG. 4 is an illustrative view of a sanitary article of an Example according to the present invention that uses the absorber of the Example shown in FIG. 1.
Figure 5:
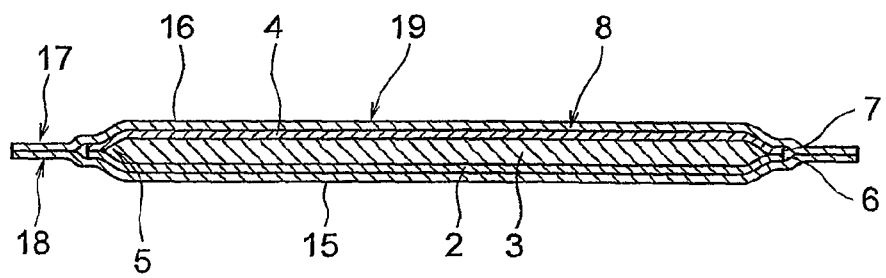
FIG. 5 is an illustrative view of a sanitary article of another Example according to the present invention that uses the absorber of the Example shown in FIG. 2.
Figure 6:
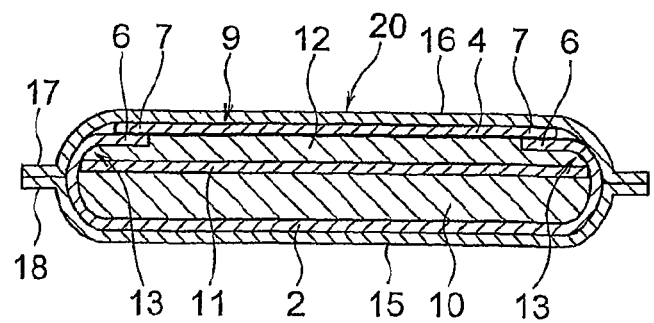
FIG. 6 is an illustrative view of a sanitary article of still another Example according to the present invention that uses the absorber of Example shown in FIG. 3.
Figure 7:
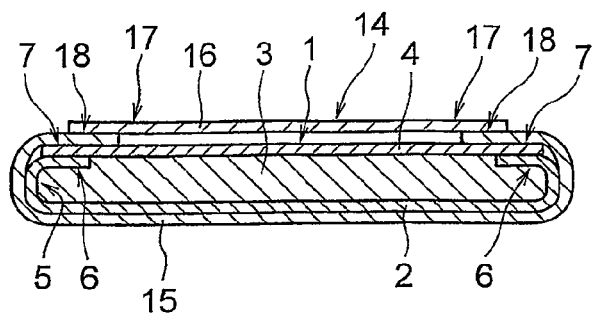
FIG. 7 is an illustrative view of a sanitary article of still another Example according to the present invention that uses the absorber of the Example shown in FIG. 1 and is different from the Example of FIG. 4.
Figure 8:
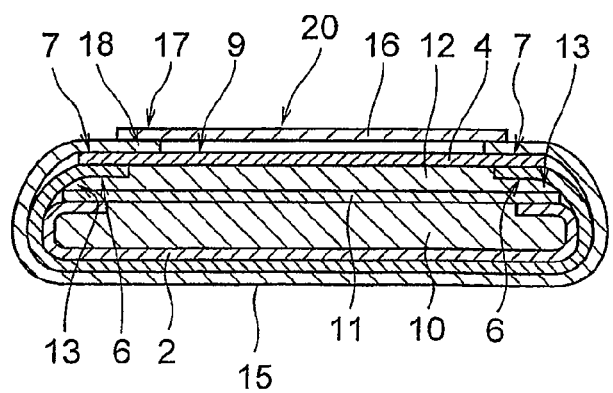
FIG. 8 is an illustrative view of a sanitary article of still another Example according to the present invention that uses the absorber of the Example shown in FIG. 3 and is different from the Example of FIG. 6.
Figure 9:
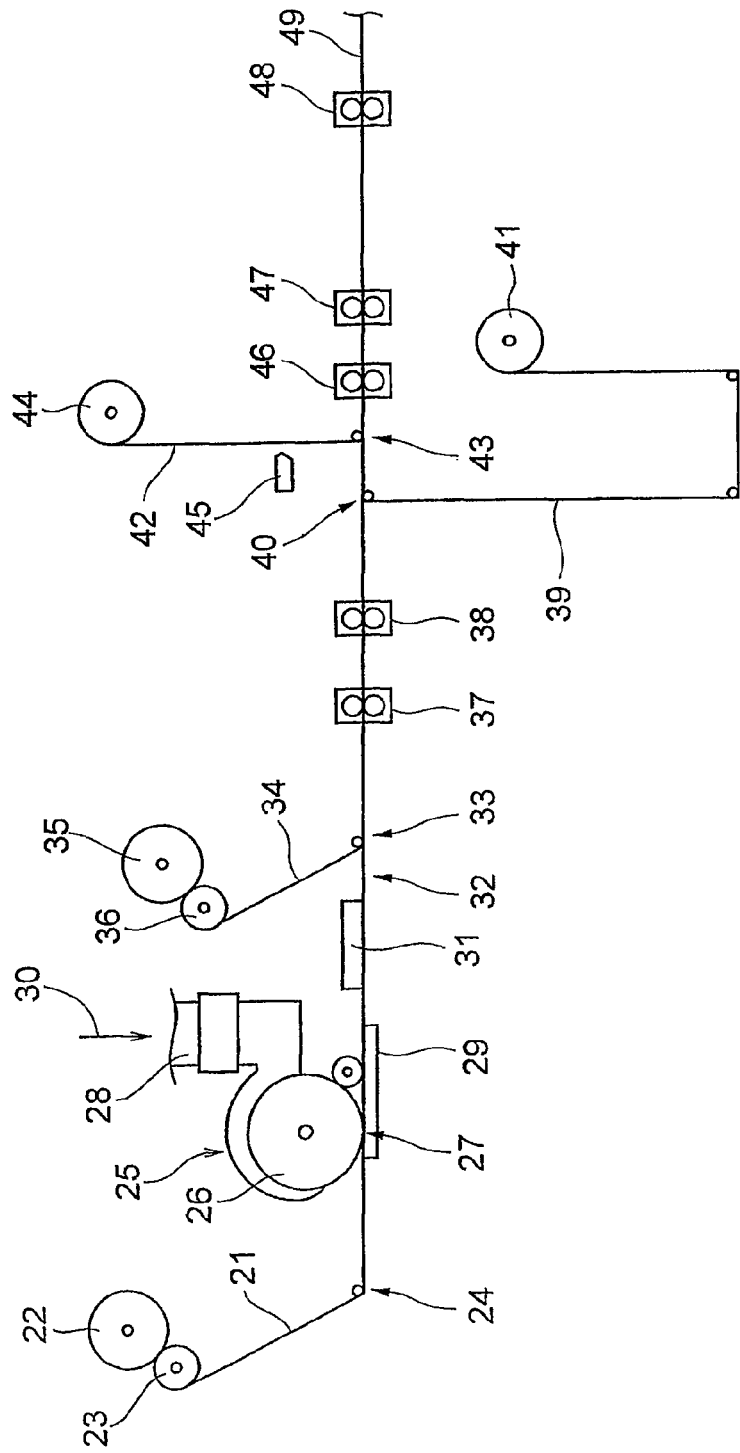
FIG. 9 is a schematic process drawing that shows the steps to produce the sanitary article of the Example shown in FIG. 4.
Figure 10:
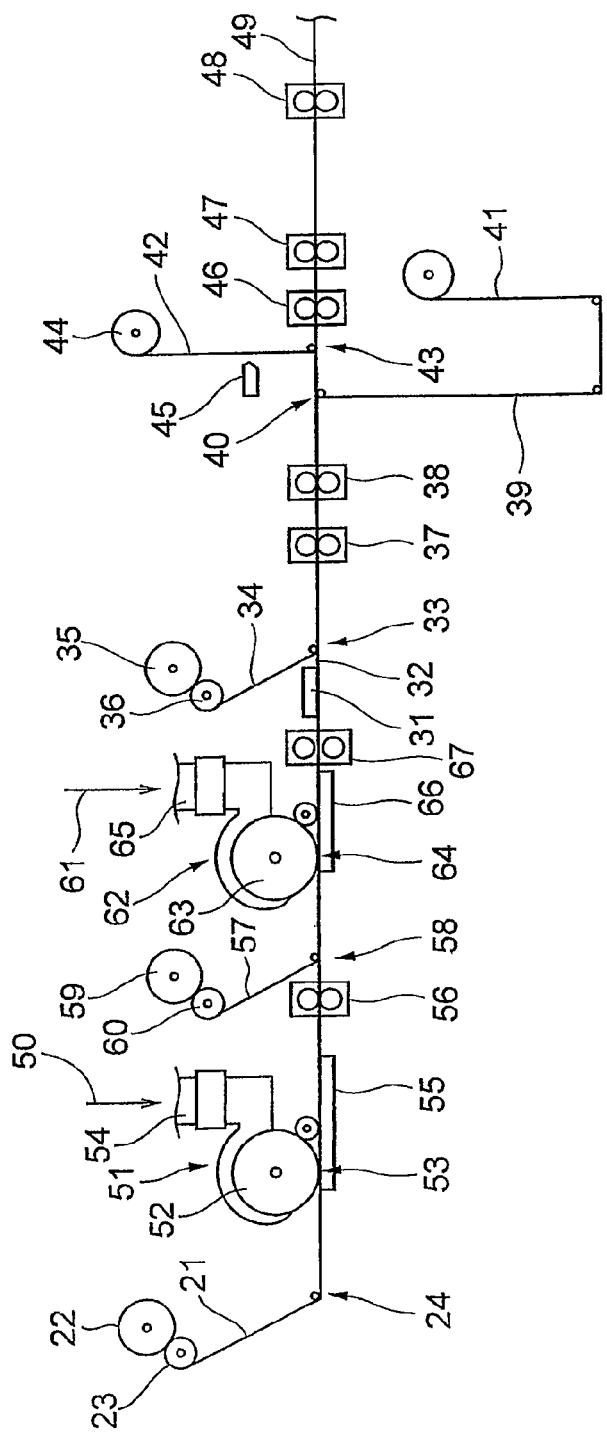
FIG. 10 is a schematic process drawing that shows the steps to produce the sanitary article of the Example shown in FIG. 6.
Figure 11:
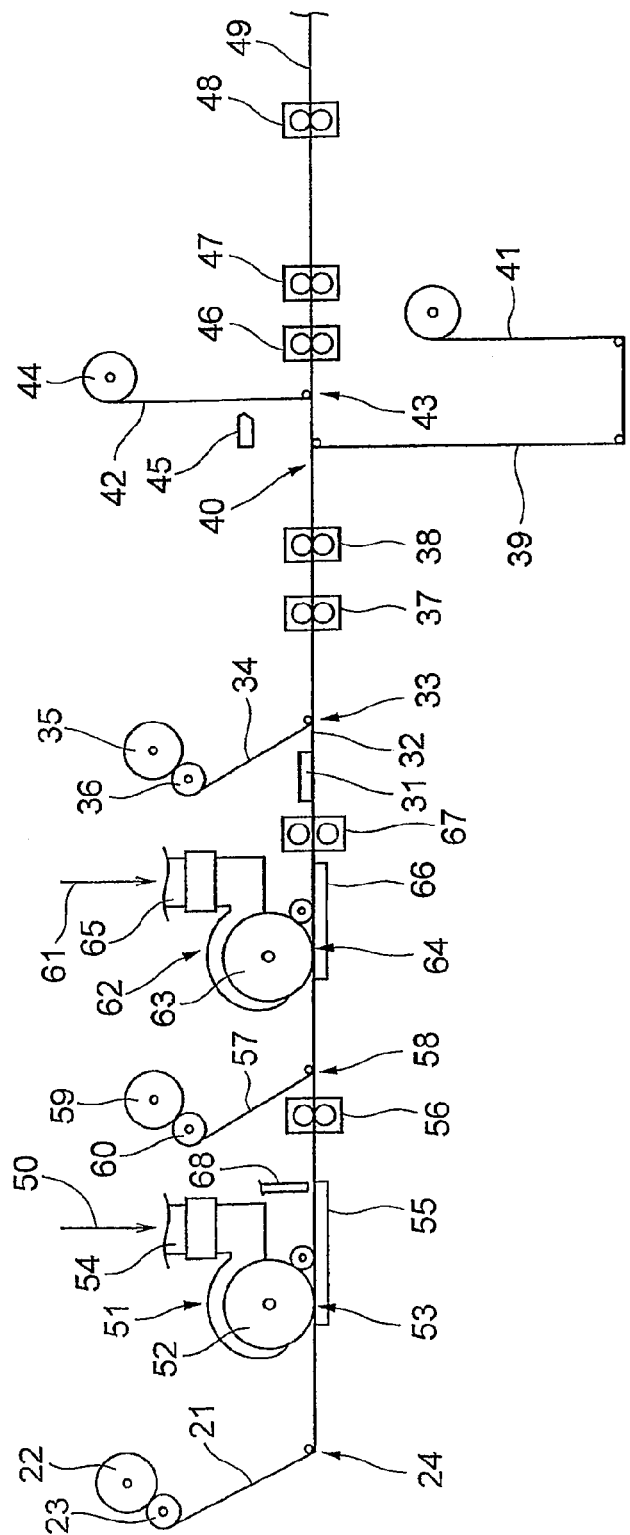
FIG. 11 is a schematic process drawing that shows the steps to produce the sanitary article of the Example shown in FIG. 6 in accordance with steps different from those of FIG. 8.

FIG. 1 is an illustrative view of an absorber of an example according to the present invention; FIG. 2 is an illustrative view of an absorber of another example according to the present invention different from the example shown in FIG. 1; FIG. 3 is an illustrative view of an absorber of still another example according to the present invention different from the examples shown in FIGS. 1 and 2; FIG. 4 is an illustrative view of a sanitary article of an example according to the present invention that uses the absorber of the example shown in FIG. 1; FIG. 5 is an illustrative view of a sanitary article of another example according to the present invention that uses the absorber of Example shown in FIG. 2; FIG. 6 is an illustrative view of a sanitary article of still another example according to the present invention that uses the absorber of Example shown in FIG. 3; FIG. 7 is an illustrative view of a sanitary article of still another example according to the present invention that uses the absorber of Example shown in FIG. 1 and is different from the example of FIG. 4; FIG. 8 is an illustrative view of a sanitary article of still another example according to the present invention that uses the absorber of Example shown in FIG. 3 and is different from the example of FIG. 6; FIG. 9 is a schematic process drawing that shows the steps to produce the sanitary article of Example shown in FIG. 4; FIG. 10 is a schematic process drawing that shows the steps to produce the sanitary article of Example shown in FIG. 6; and FIG. 11 is a schematic process drawing that shows the steps to produce the sanitary article of Example shown in FIG. 6 in accordance with steps different from those of FIG. 10. Corresponding sites are indicated using the same numbers throughout FIGS. 1 to 11.

EXAMPLE 1

The absorber of this Example is shown in FIG. 1. The absorber (1) of this Example is formed from a lower water-absorbing paper layer portion (2), a water-absorbing mixture layer portion (3), and an upper water-absorbing paper layer portion (4). The lower surface part of the absorber (1) is formed of the lower water-absorbing paper layer portion (2), and the lower water-absorbing paper layer portion (2) is formed from one or more sheet of thin paper. In this Example, the water-absorbing material mixture containing the crushed pulp fiber material beaten to have a fiber length of 0.1 to 7 mm, the crushed tea leaves having a particle size of 0.05 to 4.6 mm, and a highly water-absorbing resin in an amount less than the crushed pulp fiber material is laid on the lower water-absorbing paper layer portion (2) to form the water-absorbing mixture layer portion (3). The marginal portion (5) of the lower water-absorbing paper layer portion (2) is folded on the marginal portion (5) of the water-absorbing mixture layer portion (3) so that the formed water-absorbing mixture layer portion (3) is held by the lower water-absorbing paper layer portion (2). The marginal portion (7) of the upper water-absorbing paper layer portion (4), formed of one or more sheet of thin paper made of water-absorbing paper, is overlapped on the marginal portion (5) of the lower water-absorbing paper layer portion (2) that is folded on the marginal portion (5) of the water-absorbing mixture layer portion (3); an adhesive or tackiness agent is applied on the marginal portion (6) of the lower water-absorbing paper layer portion (2) and the marginal portion (7) of the upper water-absorbing paper layer portion (4) to adhere and fix during press-shaping by embossing, thereby the absorber (1) is formed.

In this Example, the absorber (1) forms the lower water-absorbing paper layer portion (2) by one or more sheet of thin paper on a net conveyer (not shown) equipped with a continuously moving net having a fine mesh in particular, the lower water-absorbing paper layer portion (2) is moved along with the net conveyer, the water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is supplied onto the lower water-absorbing paper layer portion (2) while aspirating from below the net conveyer by a negative pressure, and the water-absorbing mixture layer portion (3) with an entirely uniform thickness is formed on the lower water-absorbing paper layer portion (2) by applying a negative pressure from downside. In the formed water-absorbing mixture layer portion (3), the crushed tea leaves are of particles smaller than those of the crushed pulp fiber material, therefore, the crushed tea leaves migrate downward between the particles of the crushed pulp fiber material by the aspiration from downside and are dispersed denser in downside than upside within the water-absorbing mixture layer portion (3). The crushed tea leaves are dispersed as such and mostly move into the water-absorbing mixture layer portion (3), therefore, the surface of the water-absorbing mixture layer portion (3) contains less tea leaves and has a clean appearance. The marginal portion (6) of the lower water-absorbing paper layer portion (2) is folded on the marginal portion (5) of the resulting water-absorbing mixture layer portion (3), and one or more sheet of thin paper is laid on the water-absorbing mixture layer portion (3) where the marginal portion (6) of the lower water-absorbing paper layer portion (2) is folded, thereby to form the upper water-absorbing paper layer portion (4) of the upper surface part of the absorber (1). As described above, the lower water-absorbing paper layer portion (2), the water-absorbing mixture layer portion (3), and the upper water-absorbing paper layer portion (4) are laid from downside in order on the net conveyer, thus the stratified material is formed. Then the stratified material is subjected to an embossing step to undergo an embossing treatment and is integrally pressure-bonded, thereby the absorber (1) is formed in a condition that the marginal portion (7) of back and forth and around of the upper water-absorbing paper layer portion (4) is overlapped on the marginal portion (6) of back and forth and around of lower water-absorbing paper layer portion (2) and adhered, tacked, or pressure-bonded to be fixed or attached each other.

EXAMPLE 2

The absorber of this Example is shown in FIG. 2. Comparing with the absorber (1) of Example 1, the absorber (8) of this Example differs in that the marginal portion of the lower water-absorbing paper layer portion (2) is not folded on the marginal portion (5) of the water-absorbing mixture layer portion (3) and the inner face of the marginal portion (6) of the lower water-absorbing paper layer portion (2) and the inner face of the marginal portion (7) of the upper water-absorbing paper layer portion (4) are mated to be pressure-bonded or adhered; the others are similar as the absorber (1) of Example 1.

In the absorber (8) of this Example, the lower water-absorbing paper layer portion (2) is prepared by disposing one or more sheet of thin paper on a continuously moving net conveyer, the water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is supplied on the lower water-absorbing paper layer portion (2) while moving the lower water-absorbing paper layer portion (2) by the net conveyer and aspirating by a negative pressure from downside, and the water-absorbing mixture layer portion (3) with an entirely uniform thickness is formed on the lower water-absorbing paper layer portion (2) by applying a negative pressure from downside. In this Example also, the crushed tea leaves are of particles smaller than those of the crushed pulp fiber material similarly as Example 1, therefore, the crushed tea leaves migrate downward between the particles of the crushed pulp fiber material by the aspiration from downside and are dispersed denser in downside than upside within the water-absorbing mixture layer portion (3). The crushed tea leaves are dispersed as such, tea leaves are less at the surface of the water-absorbing mixture layer portion (3) and mostly exist within the water-absorbing mixture layer portion (3); therefore, the surface of the water-absorbing mixture layer portion (3) is formed with a clean appearance. One or more sheet of thin paper is laid on the water-absorbing mixture layer portion (3) formed as described above, thereby to form the upper water-absorbing paper layer portion (4) of the upper surface part of the absorber (1). The stratified material of the lower water-absorbing paper layer portion (2), the water-absorbing mixture layer portion (3), and the upper water-absorbing paper layer portion (4), formed by laying in order on the net conveyer, is subjected to an embossing step to undergo an embossing treatment and is integrally pressure-bonded, the marginal portion (7) of back and forth and around of the upper water-absorbing paper layer portion and the marginal portion (6) of back and forth and around of lower water-absorbing paper layer portion are overlapped to be pressure-bonded or adhered each other, thereby to form the absorber (1).

In Examples 1 and 2, the water-absorbing mixture layer portion (3) includes the water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material. The water-absorbing mixture layer portion (3) containing the crushed pulp fiber material, the crushed tea leaves, and the highly water-absorbing resin can be formed by disposing the mixture of the crushed pulp fiber material and the highly water-absorbing resin in an amount less than the crushed pulp fiber material with no pre-mixed crushed tea leaves on the lower water-absorbing paper layer portion on a net conveyer, spreading the crushed tea leaves over the disposed mixture of the crushed pulp fiber material and the highly water-absorbing resin, and making the particles of the crushed tea leaves migrate between the particles of the crushed pulp fiber material by action of aspiration by a negative pressure from downside of the net conveyer.

EXAMPLE 3

The absorber of this Example is shown in FIG. 3. In the absorber (9) of this Example, the lower surface part of the absorber (9) is formed of the lower water-absorbing paper layer portion (2) formed of one or more sheet of thin paper; the upper surface part is formed of the upper water-absorbing paper layer portion (4) formed of one or more sheet of thin paper; in this Example, the water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is laid on the lower water-absorbing paper layer portion (2) to form the lower water-absorbing mixture layer portion (10). An intermediate water-absorbing paper layer portion (11) formed of one or more sheet of thin paper is provided on the formed lower water-absorbing mixture layer portion (10). The water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is laid on the intermediate water-absorbing paper layer portion (11) to form the upper water-absorbing mixture layer portion (12). In this Example, the marginal portion (6) of the lower water-absorbing paper layer portion (2) is folded on the marginal portion (13) of the upper water-absorbing mixture layer portion (10) to press the marginal portion (13) of the upper water-absorbing mixture layer portion (12). The upper water-absorbing paper layer portion (4), formed of thin paper made of one or more sheet of water-absorbing paper, is formed on the upper water-absorbing mixture layer portion (12) and the marginal portion (6) of the lower water-absorbing paper layer portion (2) folded on the marginal portion (13) of the upper water-absorbing mixture layer portion (12); the marginal portion (7) of the upper water-absorbing paper layer portion (4) is adhered and fixed to the marginal portion (6) of the lower water-absorbing paper layer portion (2) during press-shaping by embossing through an adhesive or tackiness agent, thereby the absorber (1) is formed.

In the absorber (9) of this Example, the lower water-absorbing paper layer portion (2) is prepared by disposing one or more sheet of thin paper on a continuously moving net conveyer, the water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is supplied on the lower water-absorbing paper layer portion (2) while aspirating by a negative pressure from downside of the net conveyer, and the water-absorbing mixture layer portion (10) with an entirely uniform thickness is formed on the lower water-absorbing paper layer portion (2) by applying a negative pressure from downside. In this Example also, the crushed tea leaves are of particles smaller than those of the crushed pulp fiber material similarly as Examples 1 and 2, therefore, the crushed tea leaves migrate downward between the particles of the crushed pulp fiber material by the aspiration from downside and are dispersed denser in downside than upside within the water-absorbing mixture layer portion (3). The crushed tea leaves are dispersed as such, tea leaves are less at the surface of the lower water-absorbing mixture layer portion (10) and mostly exist within the lower water-absorbing mixture layer portion (10); therefore, the surface of the lower water-absorbing mixture layer portion (10) is formed with a clean appearance. One or more sheet of thin paper is laid on the lower water-absorbing mixture layer portion (10) formed as described above, thereby to form the intermediate water-absorbing paper layer portion (11). The water-absorbing material mixture containing the crushed pulp fiber material beaten to have a fiber length of 0.1 to 7 mm, the crushed tea leaves having a particle size of 0.05 to 4.6 mm, and the highly water-absorbing resin in an amount less than the crushed pulp fiber material is supplied on the intermediate water-absorbing paper layer portion (11) while aspirating by a negative pressure from downside of the net conveyer, and the upper water-absorbing mixture layer portion (12) with an entirely uniform thickness is formed on the intermediate water-absorbing paper layer portion (11) by applying a negative pressure from downside. In this Example also, the crushed tea leaves are of particles smaller than those of the crushed pulp fiber material, therefore, the crushed tea leaves migrate downward between the particles of the crushed pulp fiber material by the aspiration from downside and are dispersed denser in downside than upside within the upper water-absorbing mixture layer portion (12); and the tea leaves are less at the surface of the upper water-absorbing mixture layer portion (12) and mostly exist within the upper water-absorbing mixture layer portion (12). In this Example, the marginal portion (6) of the lower water-absorbing paper layer portion (2) formed as described above is folded on the marginal portion (11) of the upper water-absorbing mixture layer portion (12) to press the marginal portion (13) of the upper water-absorbing mixture layer portion (12), then the upper water-absorbing paper layer portion (4) is formed by disposing one or more sheet of thin paper thereon. The resulting upper water-absorbing paper layer portion (4), the upper water-absorbing mixture layer portion (12), the intermediate water-absorbing paper layer portion (11), the lower water-absorbing mixture layer portion (10), and the lower water-absorbing paper layer portion (2) are integrally pressed and shaped by embossing, and further the marginal portion (7) of back and forth and around of the upper water-absorbing paper layer portion (4) and the marginal portion (6) of back and forth and around of the lower water-absorbing paper layer portion (2) are overlapped to be pressure-bonded or adhered each other through an adhesive, thereby to form the absorber (1).

EXAMPLE 4

The sanitary article of this Example is shown in FIG. 4. The sanitary article (14) of this Example is an example where the absorber (1) prepared in Example 1 is used for the sanitary article. In the sanitary article of this Example, the absorber (1) prepared in Example 1 is disposed on a polyethylene film to form a water-impermeable film portion (15); a water-permeable layer part (14) formed of a nonwoven fabric, for example, is provided on the absorber (1) to cover the absorber (1); and the marginal portion (17) of back and forth and around of the water-permeable layer part (16) is overlapped and adhered to the marginal portion (18) of back and forth and around of the water-impermeable film portion (15), thereby to form the sanitary article (14).

EXAMPLE 5

The sanitary article of this Example is shown in FIG. 5. The sanitary article (19) of this Example is an example where the absorber (8) prepared in Example 2 is used for the sanitary article. The absorber (8) prepared in Example 2 is disposed on a polyethylene film to form a water-impermeable film portion (15). A nonwoven fabric, for example, is disposed on the absorber (8) to cover the absorber (8), and a water-permeable layer part (16) is formed on the absorber (8). The marginal portion (17) of back and forth and around of the water-permeable layer part (16) is overlapped and adhered to the marginal portion (18) of back and forth and around of the water-impermeable film portion (15), thereby to form the sanitary article (19).

EXAMPLE 6

The sanitary article of this Example is shown in FIG. 6. The sanitary article (20) of this Example is an example where the absorber (1) prepared in Example 3 is used for the sanitary article. The absorber (1) prepared in Example 3 is disposed on a polyethylene film to form a water-impermeable film portion (13); a water-permeable layer part (14) formed of a nonwoven fabric, for example, is disposed on the absorber (1) to cover the absorber (1); and the marginal portion (15) of back and forth and around of the water-permeable layer part (14) is overlapped and adhered to the marginal portion (16) of back and forth and around of the water-impermeable layer portion (13), thereby to form the sanitary article (12).

EXAMPLE 7

The sanitary article of this Example is shown in FIG. 7. The sanitary article (14) of this Example is an example where the absorber (1) prepared in Example 1 is used for the sanitary article and differs from Example 4 shown in FIG. 4 in that the water-impermeable film portion (13) is bent and its marginal portion (18) is overlapped on the marginal portion (7) of the upper water-absorbing paper layer portion (4), on which the water-permeable layer part (14) is overlapped, and the marginal portion (18) of the water-impermeable film portion (13) and the marginal portion (17) of the water-permeable layer part (14) are adhered and fixed.

In the sanitary article of this Example, the absorber (1) prepared in Example 1 is disposed on a polyethylene film to form a water-impermeable film portion (15), the marginal portion (18) of the water-impermeable film portion (15) is overlapped on the marginal portion (7) of the upper water-absorbing paper layer portion (4), on which the marginal portion (17) of the water-permeable layer part (14), formed of a nonwoven fabric for example, is overlapped to cover the absorber (1). The marginal portion (17) of back and forth and around of the overlapped water-permeable layer part (16) is adhered to the marginal portion (18) of back and forth and around of the water-impermeable film portion (15), thereby to form the sanitary article (14).

EXAMPLE 8

The sanitary article of this Example is shown in FIG. 8. The sanitary article (20) of this Example is an example where the absorber (1) prepared in Example 3 is used for the sanitary article and differs from Example 4 shown in FIG. 4 in that the marginal portion (18) of the water-impermeable film portion (13) is bent and overlapped on the marginal portion (7) of the upper water-absorbing paper layer portion (4), on which the water-permeable layer part (14) is overlapped, and the marginal portion (18) of the water-impermeable film portion (13) and the marginal portion (17) of the water-permeable layer part (14) are adhered and fixed.

In the sanitary article of this Example, the absorber (1) prepared in Example 3 is disposed on a polyethylene film to form a water-impermeable film portion (13), the marginal portion (18) of the water-impermeable film portion (15) is bent and overlapped on the marginal portion (7) of the upper water-absorbing paper layer portion (4), on which the marginal portion (17) of the water-permeable layer part (16), formed of a nonwoven fabric for example, is overlapped to cover the absorber (1). The marginal portion (17) of back and forth and around of the overlapped water-permeable layer part (16) is adhered to the marginal portion (18) of back and forth and around of the water-impermeable film portion (15), thereby to form the sanitary article (14).

EXAMPLE 9

FIG. 9 shows the steps to produce the sanitary article (14) shown in Example 4. In this Example, the lower thin paper (21) to form the lower water-absorbing paper layer portion (2) is taken out from the lower thin paper supply roll (22) by a lower thin paper-taking roller (23), ridden on a net conveyer (not shown) at the lower thin paper laying site (24), and sent to the water-absorbing material mixture laying site (27) below the supply roller (26) of the stacking machine (25) for supplying the water-absorbing material mixture. In this Example, a water-absorbing material mixture-supplying hopper (28), which connects to a crusher and a mixer (not shown), is provided above the supply roller (26) of the stacking machine (25) for supplying the water-absorbing material mixture and an aspiration box (29) to connect to an aspiration pump (not shown) is provided below the supply roller (26). In this Example, a water-absorbing material mixture (30), into which the crushed pulp fiber material having a particle size of 0.05 to 5 mm, the crushed tea leaves having a particle size of 0.05 to 3.5 mm, and the highly water-absorbing resin have been mixed in a certain ratio, is supplied to the water-absorbing material mixture-supplying hopper (28). The lower water-absorbing paper layer portion (2), on which the water-absorbing material mixture (30) has been supplied from the supply roller (26), is sent to a lower thin paper marginal portion-bending machine (31) by the net conveyer, the laid water-absorbing material mixture (30) is pressed by a press (not shown), and the marginal portion of the lower thin paper (21) is folded on the marginal portion. The marginal portion of the lower thin paper (21) is folded on the marginal portion of the water-absorbing material mixture (30) to form a sanitary article-intermediate stack (32). The sanitary article-intermediate stack (32) is sent to the upper thin paper laying site (33), and upper thin paper (34) to form the upper water-absorbing paper layer portion (4) is taken out from an upper thin paper supply roll (35) by an upper thin paper-taking roller (36) and disposed on the sanitary article-intermediate stack (32) at the upper thin paper laying site (33).

The sanitary article-intermediate stack (32), on which the upper thin paper has been laid, is sent to an embossing machine (37) and put a design thereon. The sanitary article-intermediate stack (32) with the design is sent to a mat cutter (38), and the sanitary article-intermediate stack (32) is cut into 400 mm long. The cut sanitary article-intermediate stack (32) is sent to a supply site (40) of a back film (39) to form the water-impermeable film portion (15), and a polyethylene film (39) for the back film is supplied from a polyethylene film supply roll (41) from downside. The sanitary article-intermediate stack (32), on which the polyethylene film (39) has been supplied, is disposed on a polyethylene film (40) and sent to a supply site (43) of polypropylene nonwoven fabric (42) to form the water-permeable layer part (16), to which the polypropylene nonwoven fabric (42) is supplied from upside. In this Example, the polypropylene nonwoven fabric (42) is taken out from a roll (44) of the polypropylene nonwoven fabric (42), and a hot-melt adhesive is sprayed from an atomizer (45) on the way. The polypropylene nonwoven fabric (42), to which the hot-melt adhesive has been sprayed, is ridden on the sanitary article-intermediate stack (32) and sent to a side-sealing device (46), and the both sides are pressed and attached to be adhered by the sprayed hot-melt adhesive. The sanitary article-intermediate stack (32), of which both sides have been adhered, is sent to an end-sealing device (47) to adhere the longitudinal both ends, and sent to a product cutter (48) and cut into a predetermined size and conveyed as products. The products, cut by the product cutter (30), are conveyed through a product conveying route (49), and folded up by a folding device and packaged by a packaging device (not shown), and shipped.

EXAMPLE 10

FIG. 10 shows the steps to produce the sanitary article (20) shown in Example 6. In this Example, the lower thin paper (21) to form the lower water-absorbing paper layer portion (2) is taken out from the lower thin paper supply roll (22) by a lower thin paper-taking roller (23), and ridden on a net conveyer (not shown) at the lower thin paper laying site (24). Then the lower thin paper (21) is sent to the first water-absorbing material mixture laying site (53) below the supply roller (52) of the first stacking machine (51) for supplying the first water-absorbing material mixture (50) to form the upper water-absorbing mixture layer portion. In this Example, a first water-absorbing material mixture-supplying hopper (54), which connects to a crusher and a mixer (not shown), is provided above the supply roller (52) of the first stacking machine (51) for supplying the first water-absorbing material mixture, and an aspiration box (55) to connect to an aspiration pump (not shown) is provided below the supply roller (52).

In this Example, a water-absorbing material mixture (50), into which the crushed pulp fiber material having a particle size of 0.05 to 5 mm, the crushed tea leaves having a particle size of 0.05 to 3.5 mm, and the highly water-absorbing resin have been mixed in a certain ratio, is supplied to the first water-absorbing material mixture-supplying hopper (54).

The lower thin paper (21), on which the first water-absorbing material mixture (50) has been supplied from the supply roller (52), is sent to a pressing device (56) and press-shaped together with the laid first water-absorbing material mixture (50). The lower thin paper (21), on which the press-shaped first water-absorbing material mixture (50) has been ridden, is sent to a laying site (58) of the intermediate thin paper (57) to form the intermediate water-absorbing paper layer portion (11), and intermediate thin paper (57) is taken out of an intermediate thin paper-supply roll (59) by an intermediate thin paper-taking roller (60) and disposed on the first water-absorbing material mixture (50) laid on the lower thin paper (21). The lower thin paper (21), on which the first water-absorbing material mixture on which the intermediate thin paper (57) had been disposed at the intermediate thin paper laying site (58) has been laid, is sent to the second water-absorbing material mixture laying site (64) below the supply roller (63) of the second stacking machine (62) for supplying the second water-absorbing material mixture (61) into which the crushed pulp fiber material having a particle size of 0.05 to 5 mm and the crushed tea leaves having a particle size of 0.05 to 3.5 mm have been mixed in a certain ratio to form the upper water-absorbing material layer part (12).

In this Example, a second water-absorbing material mixture-supplying hopper (65) is provided above the supply roller (63) of the second stacking machine (62) for supplying the second water-absorbing material mixture and an aspiration box (66) to connect to an aspiration pump (not shown) is provided below the supply roller (63). The lower thin paper (21), on which the second water-absorbing material mixture (61) has been supplied, is sent to the pressing device (67) by the net conveyer, and the laid second water-absorbing material mixture (61) is press-shaped. The lower thin paper (21), on which the press-shaped second water-absorbing material mixture (61) has been ridden, is sent to a lower thin paper marginal portion-bending machine (31), and the marginal portion of the lower thin paper (21) is folded on the marginal portion. The marginal portion of the lower thin paper (21) is folded on the marginal portion of the second water-absorbing material mixture (61) to form a sanitary article-intermediate stratified material (32). The sanitary article-intermediate stratified material (32) is sent to the upper thin paper laying site (33), and upper thin paper (34) to form the upper water-absorbing paper layer portion (4) is taken out from an upper thin paper supply roll (35) by an upper thin paper-taking roller (36) and disposed on the sanitary article-intermediate stratified material (32) at the upper thin paper laying site (33).

The sanitary article-intermediate stratified material (32), on which the upper thin paper has been laid, is sent to an embossing machine (37) and put a design thereon. The sanitary article-intermediate stratified material (32) with the design is sent to a mat cutter (38), and the sanitary article-intermediate stratified material (32) is cut into 400 mm long. The cut sanitary article-intermediate stratified material (32) is sent to a supply site (40) of a back film 39 to form the water-impermeable film portion (15), and a polyethylene film (39) for the back film is supplied from a polyethylene film supply roll (41) from downside. The sanitary article-intermediate stack (32), on which the polyethylene film (39) has been supplied, is disposed on a polyethylene film 40 and sent to a supply site (43) of polypropylene nonwoven fabric (42) to form the water-permeable layer part (16), to which the polypropylene nonwoven fabric 42 is supplied from upside. In this Example, the polypropylene nonwoven fabric (42) is taken out from a roll (44) of the polypropylene nonwoven fabric (42), and a hot-melt adhesive is sprayed from an atomizer (45) on the way. The polypropylene nonwoven fabric (42), to which the hot-melt adhesive has been sprayed, is ridden on the sanitary article-intermediate stratified material (32) and sent to a side-sealing device (46), and the both sides are pressed and attached to be adhered by the sprayed hot-melt adhesive. The sanitary article-intermediate stratified material (32), of which both sides have been adhered, is sent to an end-sealing device (47) to adhere the longitudinal both ends, and sent to a product cutter (48) and cut into a predetermined size and conveyed as products (49). The products (49), cut by the product cutter (48), are conveyed to a folding device (not shown) and folded by the folding device (not shown), packaged by a packaging device (not shown), and shipped.

EXAMPLE 11

Example 11 illustrates the production steps of the two-layer type sanitary article (20) shown in FIG. 6 or FIG. 8; the production steps are different from those of the sanitary article (9) shown in Example 8 in that a water-absorbing material mixture, into which the crushed pulp fiber material having a particle size of 0.05 to 5 mm and the crushed tea leaves having a particle size of 0.05 to 3.5 mm have been mixed in a certain ratio, is used as the first and the second water-absorbing material mixture to form the lower water-absorbing mixture layer portion and that the mixing of the highly water-absorbing resin into the first water-absorbing material mixture is carried out by spreading to the lower water-absorbing mixture layer portion which has been laid and formed into a constant thickness, at a highly water-absorbing resin-spreading site (68) from a highly water-absorbing resin-spreading device (69); the others are substantially the same as the production steps of the sanitary article (20) shown in Example 8.

This Example differs in that the first water-absorbing material mixture, into which the crushed pulp fiber material having a particle size of 0.05 to 5 mm, the crushed tea leaves having a particle size of 0.05 to 3.5 mm, and the highly water-absorbing resin in an amount less than the crushed pulp fiber material have been mixed in a certain ratio, and further the highly water-absorbing resin are additionally mixed by spreading from the highly water-absorbing resin-spreading device (69) at the highly water-absorbing resin-spreading site (68); the others may be substantially the same as the production steps of the sanitary article (20) shown in Example 8.

EXAMPLE 10

Example 1
(1) The thin regular-type pet sheet is, basically, 300 mm wide and 450 mm long in outer size, 300 mm wide and 400 mm long in inner size, the composition is 7 g of pulp amount, 3 g of highly water-absorbing resin amount, and 10 g of water-absorbing paper; and the total weight is 19 g.
(2) The thin wide-type pet sheet is, basically, 400 mm wide and 600 mm long in outer size, 400 mm wide and 600 mm long in inner size, the composition is 16 g of pulp amount, 5 g of highly water-absorbing resin amount, and 16 g of water-absorbing paper; and the total weight is 37 g.
(3) The thick regular-type pet sheet is, basically, 300 mm wide and 450 mm long in outer size, 300 mm wide and 400 mm long in inner size, the composition is 12 g of pulp amount, 4 g of highly water-absorbing resin amount, and 9 g of water-absorbing paper; and the total weight is 25 g.
(4) The thick wide-type pet sheet is, basically, 430 mm wide and 600 mm long in outer size, 430 mm wide and 550 mm long in inner size, the composition is 28 g of pulp amount, 5 g of highly water-absorbing resin amount, and 15 g of water-absorbing paper; and the total weight is 48 g.

(5) Basic performances as pet sheet were measured with respect to these basic-type pet sheets of thin regular-type, thin wide-type, thick regular-type, and thick wide-type. The results are shown in Table 1.

TABLE 1

|  | Thin Regular type | Thin Wide type | Thick Regular type | Thick Wide type |
|---|---|---|---|---|
| Infiltration velocity (s) | 26 | 25 | 22 | 27 |
| Drying Velocity (s) | 42 | 41 | 36 | 44 |
| Return Sheet Number (n) | 1.0 | 1.0 | 1.0 | 1.0 |
| Return Amount (g) | 0.05 | 0.07 | 0.05 | 0.07 |
| Spot Property (cm) | 18.0 | 18.3 | 13.8 | 13.4 |
| Water-Absorbing Amount (ml) | 1.271 | 2.087 | 1.684 | 2.215 |

(6) In this Example, the infiltration velocity, drying velocity, return sheet number, return amount, spot property, and water-absorbing amount are represented as follows:

That is, the infiltration velocity is represented by the period (second) from the time when 25 ml of normal saline solution of 0.9% by weight is poured to one point of central portion of a sheet until the time when a star-shape wet pattern at the poured portion spreads over the entire sheet. The drying velocity is represented by the period (second) from the time when 25 ml of normal saline solution of 0.9% by weight is poured to one point of central portion of a sheet until the time when the poured surface is dried from finger feeling. The "spot property" is obtained after measuring the drying velocity by measuring the spread dimension as to the longitudinal size in the longest spread axis and the traverse size in its perpendicular axis and is represented as: [(longitudinal size+ traverse size)×½]. The "return amount" is obtained by pouring 25 ml of normal saline solution of 0.9% by weight to one point of central portion of a sheet, allowing to stand for 3 minutes, laying 10 sheets of pre-weighed circular filter paper of diameter 110 mm on the poured site, and disposing a weight of 1.5 kg thereon to load for one minute, followed by measuring the weight of the filter paper, and is represented by the measured amount of water. The return sheet number is represented by the sheet number of filter paper that has absorbed water immediately after applying a certain weight for one minute. The water-absorbing amount is obtained by immersing perfectly a pre-weighed sheet into tap water at 20° C., taking out after 3 minutes and hanging it in a room, and measuring the weight of the sheet, and is represented by the amount of water absorbed by the sheet.

The examples shown below illustrate the cases where the degradation of water-absorbing, water-holding, and drying performances due to inclusion of crushed tea leaves is lowered in the absorber and sanitary articles using the absorber, and the cases of the absorber and sanitary articles using the absorber even containing crushed tea leaves that exhibit the infiltration velocity, drying velocity, spot property, return sheet number, and return amount comparable to the absorber and sanitary articles using the absorber containing no crushed tea leaves.

The crushed pulp fiber materials and the crushed tea leaves, contained in the absorbers and sanitary articles, are those having a particle size within a constant range, and the range of particle size and the composition of particle size are shown below.

(1) Particle Size of Pulp Fiber

The analytical results of particle size of pulp fiber used in the sanitary articles of this example are shown in Table 2.

TABLE 2

| Particle Size (mm) | % by weight |
|---|---|
| <0.05 | 2.2 |
| 0.05 to 0.3 | 4.5 |
| 0.3 to 0.7 | 4.5 |
| 0.7 to 1.1 | 5.4 |
| 1.1 to 1.5 | 5.9 |
| 1.5 to 1.9 | 9.1 |
| 1.9 to 2.3 | 10.1 |
| 2.3 to 2.7 | 10.7 |
| 2.7 to 3.1 | 13.5 |
| 3.1 to 3.5 | 13.1 |
| 3.5 to 3.9 | 10.1 |
| 3.9 to 4.3 | 3.6 |
| 4.3 to 4.7 | 1.8 |
| 4.7 to 5.1 | 0.9 |
| 5.1 to 5.5 | 1.0 |
| 5.5< | 1.8 |

(2) Preparation of Fine-Coarse Crushed Tea Leaves

The tea leaves used in this example were green tea. The tea leaves of green tea were crushed using a crusher (manufactured by Horai Co. Ltd.) so that the particles to pass through 0.05 mm mesh are 1% by weight or less, thereby preparing the fine-coarse crushed tea leaves of green tea having a particle size of 0.05 mm to 0.6 mm. The analytical result of the prepared fine-coarse crushed tea leaves of green tea is exemplarily shown in Table 3.

TABLE 3

| Particle Size (mm) | % by weight |
|---|---|
| <0.05 | — |
| 0.05 to 0.1 | 19 |
| 0.1 to 0.2 | 21 |
| 0.2 to 0.3 | 39 |
| 0.3 to 0.4 | 15 |
| 0.4 to 0.6 | 6 |
| 0.6< | — |

(3) Preparation of Medium-Coarse Crushed Tea Leaves

The tea leaves of green tea were crushed using a crusher (manufactured by Horai Co. Ltd.) so that the particles to pass through 0.7 mm mesh are 1% by weight or less, thereby preparing the medium-coarse crushed tea leaves of green tea having a particle size of 0.7 mm to 2.2 mm. The analytical result of the prepared medium-coarse crushed tea leaves of green tea is exemplarily shown in Table 4.

TABLE 4

| Particle Size (mm) | % by weight |
|---|---|
| <0.7 | 0.5 |
| 0.7 to 0.9 | 0.5 |
| 0.9 to 1.0 | 1.0 |
| 1.0 to 1.2 | 3.0 |
| 1.2 to 1.4 | 12.0 |
| 1.4 to 1.6 | 57.0 |
| 1.6 to 1.8 | 24.0 |
| 1.8 to 2.0 | 1.0 |
| 2.0 to 2.2 | 0.5 |
| 2.2< | 0.5 |

(4) Preparation of Large-Coarse Crushed Tea Leaves

The tea leaves of green tea were crushed using a crusher (manufactured by Horai Co. Ltd.) so that the particles to pass through 2.0 mm mesh are 1% by weight or less, thereby preparing the large-coarse crushed tea leaves of green tea having a particle size of 2.0 mm to 3.6 mm. The analytical result of the prepared large-coarse crushed tea leaves of green tea is exemplarily shown in Table 5.

TABLE 5

| Particle Size (mm) | % by weight |
|---|---|
| <2.0 | 0.5 |
| 2.0 to 2.4 | 1.5 |
| 2.4 to 2.8 | 6.0 |
| 2.8 to 3.0 | 24.0 |
| 3.0 to 3.2 | 48.0 |
| 3.2 to 3.4 | 15.0 |
| 3.4 to 3.6 | 4.0 |
| 3.6< | 1.0 |

(1) Example of Water-Absorbing Property of Thin Regular-Type Pet Sheet Containing Fine-Coarse Crushed Tea Leaves The thin regular-type pet sheets containing fine-coarse crushed tea leaves of examples 1 to 5 (hereinafter referred to as "crushed tea leaves" in these examples) were prepared in accordance with Example 7 described above. The thin regular-type pet sheet containing the fine-coarse crushed tea leaves of green tea of these examples is 300 mm wide and 450 mm long in outer size, and 300 mm wide and 400 mm long in inner size. In each example of the thin regular-type pet sheet, the water-permeable layer part is formed from 2.2 g of nonwoven fabric, the water-impermeable film portion is formed from 2.5 g of plastic film, the upper and lower water-absorbing paper layer portions are respectively formed from 1.7 g of thin paper, and the water-absorbing mixture layer portion is formed from a mixture of 7 g of fluff pulp obtained in a disposable diaper-production step as the crushed pulp fiber material, 3 g of the highly water-absorbing resin, and the crushed tea leaves.

Accordingly, examples 1 to 5 are different only in terms of the amount of crushed tea leaves included in the water-absorbing mixture layer portion and substantially the same in terms of the others.

That is, example 1 is a case where 1 g of fine-coarse crushed tea leaves is added to the mixture of 7 g of fluff pulp and 3 g of highly water-absorbing resin and sufficiently mixed to form the water-absorbing mixture layer portion, and the total weight as the pet sheet is 20 g; example 2 is a case where 3 g of fine-coarse crushed tea leaves is added to the mixture of 7 g of fluff pulp and 3 g of highly water-absorbing resin and sufficiently mixed to form the water-absorbing mixture layer portion, and the total weight as the pet sheet is 22 g; example 3 is a case where 5 g of fine-coarse crushed tea leaves is added to the mixture of 7 g of fluff pulp and 3 g of highly water-absorbing resin and sufficiently mixed to form the water-absorbing mixture layer portion, and the total weight as the pet sheet is 24 g; example 4 is a case where 7 g of fine-coarse crushed tea leaves is added to the mixture of 7 g of fluff pulp and 3 g of highly water-absorbing resin and sufficiently mixed to form the water-absorbing mixture layer portion, and the total weight as the pet sheet is 26 g; example 5 is a case where 10 g of fine-coarse crushed tea leaves is added to the mixture of 7 g of fluff pulp and 3 g of highly water-absorbing resin and sufficiently mixed to form the water-absorbing mixture layer portion, and the total weight as the pet sheet is 29 g. The infiltration velocity, drying velocity, return sheet number, return amount, spot property, and water-absorbing amount were measured for the respective examples similarly as reference examples. The measurement results are shown in Table 6.

TABLE 6

|  | ex. 1 | ex. 2 | ex. 3 | ex. 4 | ex. 5 |
|---|---|---|---|---|---|
| Infiltration velocity (s) | 25 | 26 | 27 | 31 | 37 |
| Drying Velocity (s) | 45 | 51 | 49 | 56 | 65 |
| Return Sheet Number (n) | 3 | 2 | 2 | 2 | 3 |
| Return Amount (g) | 0.10 | 0.14 | 0.10 | 0.15 | 0.14 |
| Spot Property (cm) | 17.2 | 17.7 | 17.5 | 17.9 | 16.1 |
| Water-Absorbing Amount (l) | 1.104 | 1.133 | 1.083 | 1.189 | 1.117 |

(2) Example of Properties of Thin Regular-Type Pet Sheet Containing Medium-Coarse Crushed Tea Leaves The thin regular-type pet sheets containing medium-coarse crushed tea leaves of examples 6 to 10 (hereinafter referred to as "crushed tea leaves" in these examples) were prepared in accordance with Example 7 described above. The thin regular-type pet sheet containing the medium-coarse crushed tea leaves of green tea of these examples is 300 mm wide and 450 mm long in outer size, and 300 mm wide and 400 mm long in inner size. In each example of the thin regular-type pet sheet, the water-permeable layer part is formed from 2.2 g of nonwoven fabric, the water-impermeable film portion is formed from 2.5 g of plastic film, the upper and lower water-absorbing paper layer portions are respectively formed from 1.7 g of thin paper, and the water-absorbing mixture layer portion is formed from a mixture of 7 g of fluff pulp obtained in a disposable diaper-production step as the crushed pulp fiber material, 3 g of the highly water-absorbing resin, and the medium-coarse crushed tea leaves.

Accordingly, examples 6 to 10 are different only in terms of the amount of medium-coarse crushed tea leaves included in the water-absorbing mixture layer portion and substantially the same in terms of the others.

That is, example 6 is a case where 1 g of medium-coarse crushed tea leaves is added to the mixture of 7 g of fluff pulp and 3 g of highly water-absorbing resin and sufficiently mixed to form the water-absorbing mixture layer portion, and the total weight as the pet sheet is 20 g; example 7 is a case where 3 g of medium-coarse crushed tea leaves is added to the mixture of 7 g of fluff pulp and 3 g of highly water-absorbing resin and sufficiently mixed to form the water-absorbing mixture layer portion, and the total weight as the pet sheet is 22 g; example 8 is a case where 5 g of medium-coarse crushed tea leaves is added to the mixture of 7 g of fluff pulp and 3 g of highly water-absorbing resin and sufficiently mixed to form the water-absorbing mixture layer portion, and the total weight as the pet sheet is 24 g; example 9 is a case where 7 g of medium-coarse crushed tea leaves is added to the mixture of 7 g of fluff pulp and 3 g of highly water-absorbing resin and sufficiently mixed to form the water-absorbing mixture layer portion, and the total weight as the pet sheet is 26 g; example 10 is a case where 10 g of medium-coarse crushed tea leaves is added to the mixture of 7 g of fluff pulp and 3 g of highly water-absorbing resin and sufficiently mixed to form the water-absorbing mixture layer portion, and the total weight as the pet sheet is 29 g. The infiltration velocity, drying velocity, return sheet number, return amount, spot property, and water-absorbing amount were measured for the respective examples similarly as reference examples. The measurement results are shown in Table 7.

TABLE 7

|  | ex. 6 | ex. 7 | ex. 8 | ex. 9 | ex. 10 |
|---|---|---|---|---|---|
| Infiltration velocity (s) | 23 | 27 | 34 | 36 | 36 |
| Drying Velocity (s) | 46 | 41 | 52 | 55 | 48 |
| Return Sheet Number (n) | 2 | 1 | 2 | 2 | 2 |
| Return Amount (g) | 0.07 | 0.08 | 0.11 | 0.12 | 0.11 |
| Spot Property (cm) | 17.8 | 18.0 | 18.3 | 16.0 | 17.1 |
| Water-Absorbing Amount (l) | 1.203 | 1.242 | 1.120 | 1.197 | 1.125 |

(3) Example of Properties of Thin Regular-Type Pet Sheet Containing Large-Coarse Crushed Tea Leaves The thin regular-type pet sheets containing medium-coarse crushed tea leaves of examples 11 to 15 (hereinafter referred to as "crushed tea leaves" in these examples) were prepared in accordance with Example 7 described above. The thin regular-type pet sheet containing the large -coarse crushed tea leaves of green tea of these examples is 300 mm wide and 450 mm long in outer size, and 300 mm wide and 400 mm long in inner size. In each example of the thin regular-type pet sheet, the water-permeable layer part is formed from 2.2 g of nonwoven fabric, the water-impermeable film portion is formed from 2.5 g of plastic film, the upper and lower water-absorbing paper layer portions are respectively formed from 1.7 g of thin paper, and the water-absorbing mixture layer portion is formed from a mixture of 7 g of fluff pulp obtained in a disposable diaper-production step as the crushed pulp fiber material, 3 g of the highly water-absorbing resin, and the large-coarse crushed tea leaves.

Accordingly, examples 11 to 15 are different only in terms of the amount of large-coarse crushed tea leaves included in the water-absorbing mixture layer portion and substantially the same in terms of the others.

That is, example 11 is a case where 1 g of large-coarse crushed tea leaves is added to the mixture of 7 g of fluff pulp and 3 g of highly water-absorbing resin and sufficiently mixed to form the water-absorbing mixture layer portion, and the total weight as the pet sheet is 20 g; example 12 is a case where 3 g of large-coarse crushed tea leaves is added to the mixture of 7 g of fluff pulp and 3 g of highly water-absorbing resin and sufficiently mixed to form the water-absorbing mixture layer portion, and the total weight as the pet sheet is 22 g; example 13 is a case where 5 g of large-coarse crushed tea leaves is added to the mixture of 7 g of fluff pulp and 3 g of highly water-absorbing resin and sufficiently mixed to form the water-absorbing mixture layer portion, and the total weight as the pet sheet is 24 g; example 14 is a case where 7 g of large-coarse crushed tea leaves is added to the mixture of 7 g of fluff pulp and 3 g of highly water-absorbing resin and sufficiently mixed to form the water-absorbing mixture layer portion, and the total weight as the pet sheet is 26 g; example 15 is a case where 10 g of large-coarse crushed tea leaves is added to the mixture of 7 g of fluff pulp and 3 g of highly water-absorbing resin and sufficiently mixed to form the water-absorbing mixture layer portion, and the total weight as the pet sheet is 29 g. The infiltration velocity, drying velocity, return sheet number, return amount, spot property, and water-absorbing amount were measured for the respective examples similarly as reference examples. The measurement results are shown in Table 8.

TABLE 8

|  | ex. 11 | ex. 12 | ex. 13 | ex. 14 | ex. 15 |
|---|---|---|---|---|---|
| Infiltration velocity (s) | 24 | 24 | 31 | 35 | 37 |
| Drying Velocity (s) | 44 | 39 | 49 | 54 | 49 |
| Return Sheet Number (n) | 2 | 1 | 2 | 3 | 3 |
| Return Amount (g) | 0.08 | 0.08 | 0.12 | 0.14 | 0.13 |
| Spot Property (cm) | 17.8 | 17.5 | 17.8 | 17.7 | 17.1 |
| Water-Absorbing Amount (l) | 1.195 | 1.072 | 1.127 | 1.104 | 1.162 |

(4) Example of Properties of Thin Wide-Type Pet Sheet Containing Fine-Coarse Crushed Tea Leaves The thin wide-type pet sheet containing fine-coarse crushed tea leaves of example 16 (hereinafter referred to as "crushed tea leaves" in this example) was prepared in accordance with Example 7 described above. The thin wide-type pet sheet containing the fine-coarse crushed tea leaves of green tea of these examples is 400 mm wide and 600 mm long in outer size, and 400 mm wide and 600 mm long in inner size. In the example 16 of the thin wide-type pet sheet, the water-permeable layer part is formed from 4 g of nonwoven fabric, the water-impermeable film portion is formed from 5 g of plastic film, the upper and lower water-absorbing paper layer portions are respectively formed from 3.5 g of thin paper, and the water-absorbing mixture layer portion is formed from a mixture of 16 g of fluff pulp obtained in a disposable diaper-production step as the crushed pulp fiber material, 5 g of the highly water-absorbing resin, and 2 g of the fine-coarse crushed tea leaves; and the total weight as the pet sheet is 39 g.

Example 17 is different from example 16 in that the amount of fine-coarse crushed tea leaves included in the water-absorbing mixture layer portion is 20 g and the total weight is 57 g as the pet sheet; the others are substantially the same.

That is, in the example 17, the water-absorbing mixture layer portion is formed by adding and sufficiently mixing 20 g of the fine-coarse crushed tea leaves to the mixture of 16 g of fluff pulp and 5 g of highly water-absorbing resin, and the total weight is 57 g as the pet sheet. In the cases of examples 16 and 17 also, the infiltration velocity, drying velocity, return sheet number, return amount, and spot property were measured similarly as reference examples. The measurement results are shown in Table 9.

TABLE 9

|  | ex. 16 | ex. 17 |
|---|---|---|
| Infiltration velocity (s) | 24 | 39 |
| Drying Velocity (s) | 46 | 69 |
| Return Sheet Number (n) | 3 | 4 |
| Return Amount (g) | 0.09 | 0.16 |
| Spot Property (cm) | 17.1 | 17.4 |

(5) Example of Properties of Thin Wide-Type Pet Sheet Containing Medium-Coarse Crushed Tea Leaves In example 18, the thin wide-type pet sheet containing medium-coarse crushed tea leaves of green tea (hereinafter referred to as "crushed tea leaves" in this example) was prepared in accordance with Example 7 described above. The thin wide-type pet sheet containing the fine-coarse crushed tea leaves of green tea of these examples is 400 mm wide and 600 mm long in outer size, and 400 mm wide and 600 mm long in inner size. In the example 18 of the thin wide-type pet sheet, the water-permeable layer part is formed from 4 g of nonwoven fabric, the water-impermeable film portion is formed from 5 g of plastic film, the upper and lower water-absorbing paper layer portions are respectively formed from 3.5 g of thin paper, and the water-absorbing mixture layer portion is formed from a mixture of 16 g of fluff pulp obtained in a disposable diaper-production step as the crushed pulp fiber material, 5 g of the highly water-absorbing resin, and 2 g of the medium-coarse crushed tea leaves; and the total weight as the pet sheet is 39 g.

Example 19 is different from example 18 in that the amount of medium-coarse crushed tea leaves included in the water-absorbing mixture layer portion is 20 g and the total weight is 57 g as the pet sheet; the others are substantially the same.

That is, in the example 19, the water-absorbing mixture layer portion is formed by adding and sufficiently mixing 20 g of the medium-coarse crushed tea leaves to the mixture of 16 g of fluff pulp and 5 g of highly water-absorbing resin, and the total weight is 57 g as the pet sheet. In the cases of examples 18 and 19 also, the infiltration velocity, drying velocity, return sheet number, return amount, and spot property were measured similarly as reference examples. The measurement results are shown in Table 10.

TABLE 10

|  | ex. 18 | ex. 19 |
| --- | --- | --- |
| Infiltration velocity (s) | 23 | 36 |
| Drying Velocity (s) | 46 | 55 |
| Return Sheet Number (n) | 2 | 3 |
| Return Amount (g) | 0.07 | 0.14 |
| Spot Property (cm) | 17.9 | 17.4 |

(6) Example of Properties of Thin Wide-Type Pet Sheet Containing Large-Coarse Crushed Tea Leaves The thin wide-type pet sheet containing large-coarse crushed tea leaves of example 20 (hereinafter referred to as "crushed tea leaves" in this example) was prepared in accordance with Example 7 described above. The thin wide-type pet sheet containing the large-coarse crushed tea leaves of green tea of these examples is 400 mm wide and 600 mm long in outer size, and 400 mm wide and 600 mm long in inner size. In the example 20 of the thin wide-type pet sheet, the water-permeable layer part is formed from 4 g of nonwoven fabric, the water-impermeable film portion is formed from 5 g of plastic film, the upper and lower water-absorbing paper layer portions are respectively formed from 3.5 g of thin paper, and the water-absorbing mixture layer portion is formed from a mixture of 16 g of fluff pulp obtained in a disposable diaper-production step as the crushed pulp fiber material, 5 g of the highly water-absorbing resin, and 2 g of the large-coarse crushed tea leaves; and the total weight as the pet sheet is 39 g.

Example 21 is different from example 20 in that the amount of large-coarse crushed tea leaves included in the water-absorbing mixture layer portion is 20 g and the total weight is 57 g as the pet sheet; the others are substantially the same.

That is, in the example 21, the water-absorbing mixture layer portion is formed by adding and sufficiently mixing 20 g of the large-coarse crushed tea leaves to the mixture of 16 g of fluff pulp and 5 g of highly water-absorbing resin, and the total weight is 57 g as the pet sheet. In the cases of examples 20 and 21 also, the infiltration velocity, drying velocity, return sheet number, return amount, and spot property were measured similarly as reference examples. The measurement results are shown in Table 11.

TABLE 11

|  | ex. 20 | ex. 21 |
| --- | --- | --- |
| Infiltration velocity (s) | 24 | 37 |
| Drying Velocity (s) | 44 | 55 |
| Return Sheet Number (n) | 2 | 4 |
| Return Amount (g) | 0.09 | 0.14 |
| Spot Property (cm) | 17.9 | 17.4 |

(7) Example of Properties of Sanitary Article for Adult Flat-Type Disposable Diaper Containing Medium-Coarse Crushed Tea Leaves Example 22 is an illustrative case of sanitary article for adult flat-type disposable diaper containing medium-coarse crushed tea leaves, the outer size is 300 mm wide and 720 mm long, the inner size is 298 mm wide and 670 mm long, and the total weight is 73 g; the sheet was prepared in accordance with Example 7. In the sanitary article, the water-permeable layer part to form the upper surface is formed of a nonwoven fabric of 300 mm wide and 720 mm long, and the weight of the nonwoven fabric is 3.9 g; on the other hand, the water-impermeable layer portion to form the lower surface is formed of a plastic film of 360 mm wide and 720 mm long, and the weight of the plastic film is 4.8 g. The upper water-absorbing paper layer portion beneath and adjoining the water-permeable layer part is formed of upper thin paper of 290 mm wide and 670 mm long, and the weight of the upper thin paper is 2.9 g; the lower water-absorbing paper layer portion disposed on the plastic film is formed of lower thin paper of 340 mm wide and 670 mm long, and the weight of the lower thin paper is 3.4 g. The water-absorbing mixture layer portion, provided between the upper and the lower water-absorbing paper layer portions, is formed from a mixture of 49.0 g of fluff pulp obtained in a disposable diaper-production step as the crushed pulp fiber material, 3 g of the highly water-absorbing resin, and 5 g of the medium-coarse crushed tea leaves of green tea. The weight of the hot-melt adhesive coated on the nonwoven fabric is 1 g.

Reference example 2 of sanitary article for adult flat-type disposable diaper was prepared in the same specifications as this example except that no crushed tea leaves are mixed and the total weight is 68 g.

Example 23 is an illustrative case of sanitary article for adult flat-type disposable diaper in which an intermediate paper layer part is provided in addition to the upper and the lower water-absorbing paper layer portions, an upper water-absorbing paper layer portion is provided between the upper water-absorbing paper layer portion and the intermediate paper layer part, and a lower water-absorbing mixture layer portion is provided between the intermediate water-absorbing paper layer portion and the lower water-absorbing paper layer portion; the upper and the lower water-absorbing mixture layer portions contain the medium-coarse crushed tea leaves of green tea; the outer size is 300 mm wide and 720 mm long, the inner size is 298 mm wide and 670 mm long; the total weight is 75 g and the sheet was prepared in accordance with Example 8.

That is, in the sanitary article of this example, the water-permeable layer part to form the upper surface is formed of a nonwoven fabric of 300 mm wide and 720 mm long, and the weight of the nonwoven fabric is 4.3 g; on the other hand, the water-impermeable layer portion to form the lower surface is formed of a plastic film of 360 mm wide and 720 mm long, and the weight of the plastic film is 4.8 g. The upper water-absorbing paper layer portion beneath and adjoining the water-permeable layer part is formed of upper thin paper of 290 mm wide and 670 mm long, and the weight of the upper thin paper is 2.9 g; the lower water-absorbing paper layer portion disposed on the plastic film is formed of lower thin paper of 340 mm wide and 670 mm long, and the weight of the lower thin paper is 3.4 g. In this example, an intermediate water-absorbing paper layer portion is provided between the upper and the lower water-absorbing paper layer portions. The intermediate water-absorbing paper layer portion is formed of an intermediate thin paper of 290 wide and 670 mm long, and the weight of the intermediate thin paper is 2.9 g. The upper water-absorbing mixture layer portion, provided between the upper water-absorbing paper layer portion and the intermediate water-absorbing paper layer portion, is formed of 26.0 g of fluff pulp obtained in a disposable diaper-production step as the crushed pulp fiber material. In addition, the lower water-absorbing mixture layer portion, provided between the intermediate and the lower water-absorbing paper layer portions, is formed from 29.5 g of the mixture of 17.5 g of fluff pulp obtained in a disposable diaper-production step as the crushed pulp fiber material, 7 weight parts of the highly water-absorbing resin, and 5 weight parts of the medium-coarse crushed tea leaves of green tea. The weight of the hot-melt adhesive coated on the nonwoven fabric is 1 g.

Reference example 3 of sanitary article for adult flat-type disposable diaper was prepared in the same specifications as this example except that no crushed tea leaves are mixed and the total weight is 70 g.

Example 24 is an illustrative case of sanitary article for adult flat-type disposable diaper in which an upper, an intermediate, and a lower water-absorbing paper layer portions are provided, an upper water-absorbing paper layer portion is provided between the upper water-absorbing paper layer portion and the intermediate paper layer part, and a lower water-absorbing mixture layer portion is provided between the intermediate water-absorbing paper layer portion and the lower water-absorbing paper layer portion; the upper and the lower water-absorbing mixture layer portions contain the medium-coarse crushed tea leaves of green tea; the outer size is 330 mm wide and 750 mm long, the inner size is 328 mm wide and 700 mm long; the total weight is 105 g and the sheet was prepared in accordance with Example 8.

That is, in the sanitary article of this example, the water-permeable layer part to form the upper surface is formed of a nonwoven fabric of 330 mm wide and 750 mm long, and the weight of the nonwoven fabric is 4.8 g; on the other hand, the water-impermeable layer portion to form the lower surface is formed of a plastic film of 385 mm wide and 700 mm long, and the weight of the plastic film is 5.1 g. The upper thin paper beneath and adjoining the water-permeable layer part is formed of upper thin paper of 320 mm wide and 700 mm long, and the weight of the upper thin paper is 3.2 g; the lower water-absorbing paper layer portion disposed on the plastic film is formed of lower thin paper of 380 mm wide and 700 mm long, and the weight of the lower thin paper is 3.8 g, the intermediate water-absorbing paper layer portion is formed of an intermediate thin paper of 320 mm wide and 700 mm long, and the weight of the intermediate thin paper is 3.2 g. The upper water-absorbing mixture layer portion, provided between the upper water-absorbing paper layer portion and the intermediate water-absorbing paper layer portion, is formed of 41.3 g of fluff pulp obtained in a disposable diaper-production step as the crushed pulp fiber material. In addition, the lower water-absorbing mixture layer portion, provided between the intermediate and the lower water-absorbing paper layer portions, is formed from 37.6 g of the mixture of 12.6 g of fluff pulp obtained in a disposable diaper-production step as the crushed pulp fiber material, 10 g of the highly water-absorbing resin, and 5 g of the medium-coarse crushed tea leaves of green tea.

Reference example 4 of sanitary article for adult flat-type disposable diaper was prepared in the same specifications as this example except that no crushed tea leaves are mixed and the total weight is 100 g.

The drying velocity, return amount, and water-absorbing amount were measured respectively with respect to examples 22, 23, and 24 and reference examples 2, 3, and 4. The measurement results (average values) are shown in Table 12.

TABLE 12

|  | ex. 22 | reference ex. 2 | ex. 23 | reference ex. 3 | ex. 24 | reference ex. 4 |
| --- | --- | --- | --- | --- | --- | --- |
| Drying Velocity (s) | 91.0 | 74.6 | 46.6 | 43.6 | 43.4 | 40.0 |
| Return Amount (g) | 0.36 | 0.25 | 0.16 | 0.12 | 0.09 | 0.11 |
| Water-Absorbing Amount (ml) | 1700 | 1700 | 2500 | 2500 | 3247 | 3247 |

(8) Example of Properties of Absorber Containing Medium-Coarse Crushed Tea Leaves An absorber containing medium-coarse crushed tea leaves of green tea (hereinafter referred to as "crushed tea leaves" in this example) of example 25 was prepared in accordance with Example 1 described above. The absorber containing medium-coarse crushed tea leaves of this example is formed into an approximate quadrangle in the size of 300 mm wide and 400 mm long. In this absorber, the upper water-absorbing paper layer portion to form the upper surface is formed of approximate quadrangle blue thin paper in the size of 275 mm wide and 400 mm long, and the weight is 1.6 g; and the lower water-absorbing paper layer portion to form the lower surface is formed of approximate quadrangle white thin paper in the size of 340 mm wide and 400 mm long, and the weight is 2.0 g. In this case, the water-absorbing mixture layer portion, provided between the upper and the lower water-absorbing paper layer portions, is formed from the mixture of 107.9 g of the crushed waste disposable diaper containing 19.41% by weight of plastic, 9.3% by weight of highly water-absorbing resin, and 71.3% by weight of fluff pulp; 3 g of highly water-absorbing resin, and the medium-coarse crushed tea leaves of green tea; and the total weight of the absorber is 119.5 g. In the example 25 also, the drying velocity, return amount, and water-absorbing amount were measured similarly as reference examples. The measurement results are shown in Table 12.

TABLE 13

|  | ex. 25 |
| --- | --- |
| Drying Velocity (s) | 310 |
| Return Amount (g) | 0.22 |
| Water-Absorbing Amount (ml) | 4700 |

The degradation of water-absorbing property of absorbers and sanitary articles due to mixing the crushed tea leaves can be reduced by excluding the interfusion of fine particles of the crushed tea leaves and can also be reduced by increasing the amount of the highly water-absorbing resin. When the water-absorbing mixture layer portion is made into two layers by providing an intermediate water-absorbing paper layer portion, it is preferred that crushed pulp fiber material is added to the upper water-absorbing mixture layer portion and highly water-absorbing resin and crushed tea leaves are added to the lower water-absorbing mixture layer portion. When crushed tea leaves are added to the upper water-absorbing mixture layer portion, the water-absorbing velocity, i.e. infiltration velocity, can be increased by decreasing the mixing amount at upper side.

EXAMPLE 11

The thin regular-type pet sheet of 300 mm wide and 450 mm long in outer size and 300 mm wide and 400 mm long in inner size was examined for the water-absorbing performance as sanitary article while maintaining the compositions of pulp amount 7 g, highly water-absorbing resin amount 3 g, and water-absorbing paper 10 g of other than crashed tea leaves and changing the mixing amount of crushed tea leaves.

(1) Infiltration Velocity

It has been found from the examples described above that when the mixing amount of crushed tea leaves was 1 g, the infiltration velocity was the highest for the article mixed with medium-coarse crushed tea leaves (hereinafter referred to as "medium-coarse mixture"), secondly high for the article mixed with large-coarse crushed tea leaves (hereinafter referred to as "large-coarse mixture"), and the lowest for the article mixed with large-coarse crushed tea leaves (hereinafter referred to as "fine-coarse mixture"). When the mixing amount of tea leaves was 3 g, the infiltration velocity was the highest for the fine-coarse mixture, secondly high for the large-coarse mixture, and the lowest for the medium-coarse mixture. When the mixing amount of tea leaves was 5 g, the infiltration velocity was the highest for the large-coarse mixture, secondly high for the fine-coarse mixture, and the lowest for the medium-coarse mixture. When the mixing amount of tea leaves was 7 g, the infiltration velocity was the highest for the fine-coarse mixture, secondly high for the large-coarse mixture, and the lowest for the medium-coarse mixture. When the mixing amount of tea leaves was 10 g, the infiltration velocity was the highest for the medium-coarse mixture, secondly high for the large-coarse mixture, and the lowest for the fine-coarse mixture.

(2) Drying Velocity

It has been found from the examples described above that when the mixing amount of crushed tea leaves was 1 g, the drying velocity was the highest for the large-coarse mixture, secondly high for the fine-coarse mixture, and the lowest for the medium-coarse mixture. When the mixing amount of crushed tea leaves was 3 g, the drying velocity was the highest for the large-coarse mixture, secondly high for the medium-coarse mixture, and the lowest for the fine-coarse mixture. When the mixing amount of crushed tea leaves was 5 g, the drying velocity was the highest for the large-coarse mixture, secondly high for the fine-coarse mixture, and the lowest for the medium-coarse mixture. When the mixing amount of crushed tea leaves was 7 g, the drying velocity was the highest for the large-coarse mixture, secondly high for the medium-coarse mixture, and the lowest for the fine-coarse mixture. When the mixing amount of crushed tea leaves was 10 g, the drying velocity was the highest for the medium-coarse mixture, secondly high for the large-coarse mixture, and the lowest for the fine-coarse mixture.

(3) Return Sheet Number

It has been found from the examples described above that when the mixing amount of crushed tea leaves was 1 g, the return sheet number was the highest for the large-coarse mixture, secondly high for the medium-coarse mixture, and the lowest for the fine-coarse mixture. When the mixing amount of crushed tea leaves was 3 g, the return sheet number was the highest for the large-coarse mixture, secondly high for the medium-coarse mixture, and the lowest for the fine-coarse mixture. When the mixing amount of crushed tea leaves was 5 g, the return sheet number was the highest for the fine-coarse mixture, secondly high for the medium-coarse mixture, and the lowest for the fine-coarse mixture. When the mixing amount of crushed tea leaves was 7 g, the return sheet number was the highest for the medium-coarse mixture, secondly high for the fine-coarse mixture, and the lowest for the large-coarse mixture. When the mixing amount of crushed tea leaves was 10 g, the return sheet number was the highest for the medium-coarse mixture, secondly high for the large-coarse mixture, and the lowest for the fine-coarse mixture.

(4) Return Amount

It has been found from the examples described above that when the mixing amount of crushed tea leaves was 1 g, the return amount was the highest for the medium-coarse mixture, secondly high for the medium-coarse mixture, and the lowest for the fine-coarse mixture. When the mixing amount of crushed tea leaves was 3 g, the return amount was the highest for the medium-coarse mixture, secondly high for the large-coarse mixture, and the lowest for the fine-coarse mixture. When the mixing amount of crushed tea leaves was 5 g, the return amount was the highest for the fine-coarse mixture, secondly high for the medium-coarse mixture, and the lowest for the large-coarse mixture. When the mixing amount of crushed tea leaves was 7 g, the return amount was the highest for the medium-coarse mixture, secondly high for the large-coarse mixture, and the lowest for the fine-coarse mixture. When the mixing amount of crushed tea leaves was 10 g, the return amount was the highest for the medium-coarse mixture, secondly high for the large-coarse mixture, and the lowest for the fine-coarse mixture.

(5) Spot Property

It has been found from the examples described above that when the mixing amount of crushed tea leaves was 1 g, the spot property was the highest for the fine-coarse mixture, secondly high for the medium-coarse mixture, and the lowest for the large-coarse mixture. When the mixing amount of crushed tea leaves was 3 g, the spot property was the highest for the large-coarse mixture, secondly high for the fine-coarse mixture, and the lowest for the medium-coarse mixture. When the mixing amount of crushed tea leaves was 5 g, the spot property was the highest for the fine-coarse mixture, secondly high for the large-coarse mixture, and the lowest for the medium-coarse mixture. When the mixing amount of crushed tea leaves was 7 g, the spot property was the highest for the medium-coarse mixture, secondly high for the large-coarse mixture, and the lowest for the fine-coarse mixture. When the mixing amount of crushed tea leaves was 10 g, the spot property was the highest for the fine-coarse mixture, secondly high for the large-coarse mixture, and the lowest for the medium-coarse mixture.

The particle size, etc. of crushed tea leaves suited to sanitary articles can be found by trial in accordance with the examples described above.

In cases of disposable diaper, urine pad, pet sheet, and sanitary napkin having the water-absorbing mixture layer portion of one layer, the particle size of crushed tea leaves is preferably a medium-coarse mixture, more preferably a large-coarse mixture. In cases of disposable diaper, urine pad, pet sheet, and sanitary napkin having the water-absorbing mixture layer portion of two layer, when the upper and the lower layers are of the same crushed tea leaves, the particle size of crushed tea leaves is preferably a medium-coarse mixture, more preferably a large-coarse mixture; when the upper and the lower layers are of the different particle size, it is preferred that the upper water-absorbing mixture layer portion is made of a large-coarse mixture and the lower water-absorbing mixture layer portion is made of a large-coarse mixture.

INDUSTRIAL APPLICABILITY

The absorber of the present invention is formed with one or more layer of water-absorbing mixture layer portion formed from the water-absorbing material mixture that contains a crushed pulp fiber material beaten to have a fiber length of 0.1 to 7 mm, crushed tea leaves having a particle size of 0.05 to 4.6 mm, and a water-absorbing resin in an amount less than the crushed pulp fiber material and contains substantially no fine particles within the crushed pulp fiber material and the crushed tea leaves particles; therefore, the crushed tea leaves particles can be mixed into the mixture of the water-absorbing resin and the crushed pulp material without separating, thus when used for disposable diaper or sanitary article, the absorber can inhibit microorganism proliferation and eliminate odor for 48 hours or more after use and can widely maintain sanitary conditions, for example. Furthermore, the sanitary articles using the absorber can exhibit water-absorbing properties such as water-absorbing, infiltrating, and drying performances in a level comparable with those non-mixing the crushed tea leaves as sanitary articles and also show proper appearance and visual quality, thus have great industrial applicability.

The invention claimed is:

1. An absorber formed integrally by overlapping in layers with an upper water-absorbing paper layer portion comprised of an upper surface, a lower water-absorbing paper layer portion comprised of a lower surface, and a water-absorbing mixture layer portion provided between the upper water-absorbing paper layer portion and the lower water-absorbing paper layer portion;
   wherein the water-absorbing mixture layer portion is comprised of a crushed pulp fiber material beaten to fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material, and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity.

2. An absorber formed integrally by overlapping in layers with an upper water-absorbing paper layer portion comprising an upper surface, a lower water-absorbing paper layer portion comprised of a lower surface, and a water-absorbing mixture layer portion provided between the upper water-absorbing paper layer portion and the lower water-absorbing paper layer portion;
   wherein the water-absorbing mixture layer portion is comprised of a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, a crushed plastic-containing material in an amount less than the crushed pulp fiber material, and a water-absorbing resin in an amount less than the crushed pulp fiber material, and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity.

3. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion, and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;
   wherein the upper water-absorbing mixture layer portion is comprised of a crushed pulp fiber material beaten to a fiber length of 0.1 to 7 mm, and the lower water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material; and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity; and
   the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

4. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;
   wherein the upper water-absorbing mixture layer portion is comprised of a crushed pulp fiber material beaten to a fiber length of 0.1 to 7 mm, and the lower water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, a crushed plastic-containing material in an amount less than the crushed pulp fiber material, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material; and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

5. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, in an amount less than the crushed pulp fiber material, and the lower water-absorbing mixture layer portion is comprised of a mixture containing a crushed pulp fiber material beaten to have a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material; and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

6. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm and crushed tea dregs having a particle size of 0.7 to 3.8 mm in mixing content percentage of 14 to 43% by weight, based on the crushed pulp fiber material as dry weight, in an amount less than the crushed pulp fiber material; and the lower water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, a crushed plastic-containing material in an amount less than the crushed pulp fiber material, and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

7. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, in an amount less than the crushed pulp fiber material, and a crushed plastic-containing material in an amount less than the crushed pulp fiber material; and the lower water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material; and the particles of crushed tea dregs are distributed so that the content increases from upper to lower within the water-absorbing mixture layer portion, and an upper water-absorbing paper layer portion, a water absorbing mixture layer portion and a lower water-absorbing paper layer portion are press-shaped integrally by overlapping in layers, to contain crushed tea dregs and to have large infiltration velocity and large drying velocity; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

8. An absorber comprising an upper water-absorbing paper layer portion comprised of an upper surface, a lower water-absorbing paper layer portion comprised of a lower surface, an intermediate water-absorbing paper layer portion provided between the upper water-absorbing paper layer portion and the lower water-absorbing paper layer portion, an upper water-absorbing mixture layer portion provided between the upper water-absorbing paper layer portion and the intermediate water-absorbing paper layer portion, and a lower water-absorbing mixture layer portion provided between the lower water-absorbing paper layer portion and the intermediate water-absorbing paper layer portion;

wherein the upper water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, in an amount less than the crushed pulp fiber material, and a crushed plastic-containing material in an amount less than the crushed pulp fiber material; and the lower water-absorbing mixture layer portion is comprised of a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, a crushed plastic-containing material in an amount less than the crushed pulp fiber material, and the particles of crushed tea dregs are distributed so that the content increases from upper to lower within the water-absorbing mixture layer portion, and an upper water-absorbing paper layer portion, a water absorbing mixture layer portion and lower water-absorbing paper layer portion are pressed-shaped integrally by overlapping in layers, to contain crushed tea dregs and to have large infiltration velocity and large drying velocity and a water-absorbing resin in an amount less than the crushed pulp fiber material; and the upper water-absorbing paper layer portion, the intermediate water-absorbing paper layer portion, the lower water-absorbing paper layer portion, the upper water-absorbing mixture layer portion, and the lower water-absorbing mixture layer portion are overlapped in layers and formed integrally.

9. A sanitary article comprising a water-permeable layer part comprised of an upper surface and a plastic water-impermeable film portion comprised of a lower surface, wherein the absorber according to claim 1 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

10. A method of producing an absorber which comprises forming a water-absorbing mixture layer portion by disposing a mixture containing a crushed pulp fiber material beaten to a fiber length of 0.1 to 7 mm in content percentage of not more than 5 weight % of fine particle with particle size of less than 0.1 mm, crushed tea dregs having a particle size of 0.7 to 3.8 mm in mixing content percentage of 14 to 43% by weight, based on the crushed pulp fiber material as dry weight, and a water-absorbing resin in an amount less than the crushed pulp fiber material on a lower water-absorbing paper layer portion formed by at least one sheet of water-absorbing paper while aspirating from below the lower water-absorbing paper layer portion;

mixing the particle of the crushed tea dregs with the crushed pulp fibber material and the water-absorbing resin, and moving the particles of the crushed tea dregs between the particles of the pulp fiber material downward and forming the water absorbing mixture layer portion in which the contents of the particles of tea dregs is distributed to increase from upper to lower, forming an upper water-absorbing paper layer portion by disposing at least one sheet of water-absorbing paper on the water-absorbing mixture layer portion;

forming a stratified material by overlapping the upper water-absorbing paper layer portion, the water-absorbing mixture layer portion, and the lower water-absorbing paper layer portion; and press-shaping integrally the stratified material to contain crushed tea dregs and to have large infiltration velocity and large drying velocity.

11. A method of producing a sanitary article which comprises forming a water-impermeable film portion in contact with the lower surface of the lower water-absorbing paper layer portion of the absorber by disposing the absorber produced by the method for producing an absorber according to claim 10, on a plastic water-impermeable film member, and forming a water-permeable layer part in contact with the upper surface of the upper water-absorbing paper layer portion of the absorber, by disposing a water-permeable porous member on the absorber.

12. A sanitary article comprising a water-permeable layer part comprised of an upper surface and a plastic water-impermeable film portion comprised of a lower surface, wherein the absorber according to claim 2 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

13. A sanitary article comprising a water-permeable layer part comprised of an upper surface and a plastic water-impermeable film portion comprised of a lower surface, wherein the absorber according to claim 3 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

14. A sanitary article comprising a water-permeable layer part comprised of an upper surface and a plastic water-impermeable film portion comprised of a lower surface, wherein the absorber according to claim 4 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

15. A sanitary article comprising a water-permeable layer part comprised of an upper surface and a plastic water-impermeable film portion comprised of a lower surface, wherein the absorber according to claim 5 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

16. A sanitary article comprising a water-permeable layer part comprised of an upper surface and a plastic water-impermeable film portion comprised of a lower surface, wherein the absorber according to claim 6 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

17. A sanitary article comprising a water-permeable layer part comprised of an upper surface and a plastic water-impermeable film portion comprised of a lower surface, wherein the absorber according to claim 7 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

18. A sanitary article comprising a water-permeable layer part comprised of an upper surface and a plastic water-impermeable film portion comprised of a lower surface, wherein the absorber according to claim 8 is disposed between the water-permeable layer part and the plastic water-impermeable film portion and the absorber is overlapped between the upper water-absorbing paper layer portion and lower water-absorbing paper layer portion so that the upper water-absorbing paper layer portion of the absorber contacts with the lower surface of the water-permeable layer part and the lower water-absorbing paper layer portion of the absorber contacts with the upper surface of the water-impermeable film portion.

\* \* \* \* \*

UNITED STATES PATENT AND TRADEMARK OFFICE
CERTIFICATE OF CORRECTION

PATENT NO.        : 8,581,018 B2
APPLICATION NO.   : 12/529028
DATED             : November 12, 2013
INVENTOR(S)       : Ito et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1075 days.

Signed and Sealed this
Twenty-second Day of September, 2015

Michelle K. Lee
*Director of the United States Patent and Trademark Office*